(12) United States Patent
Sasaki et al.

(10) Patent No.: US 9,199,024 B2
(45) Date of Patent: Dec. 1, 2015

(54) HEMODIALYSIS SYSTEM

(75) Inventors: Masatomi Sasaki, Tokyo (JP); Toru Shinzato, Toyohashi (JP); Masayo Maruyama, Toyohashi (JP); Masamiki Miwa, Toyohashi (JP)

(73) Assignees: ASAHI KASEI MEDICAL CO., LTD., Tokyo (JP); NEXTIER CORPORATION, Aichi (JP)

( * ) Notice: Subject to any disclaimer, the term of this patent is extended or adjusted under 35 U.S.C. 154(b) by 321 days.

(21) Appl. No.: 13/808,288

(22) PCT Filed: Jul. 14, 2011

(86) PCT No.: PCT/JP2011/066145
§ 371 (c)(1),
(2), (4) Date: Feb. 27, 2013

(87) PCT Pub. No.: WO2012/008544
PCT Pub. Date: Jan. 19, 2012

(65) Prior Publication Data
US 2013/0158461 A1 Jun. 20, 2013

(30) Foreign Application Priority Data
Jul. 14, 2010 (JP) .................................. 2010-160099

(51) Int. Cl.
*A61M 1/16* (2006.01)
*A61M 1/30* (2006.01)
*A61M 1/36* (2006.01)

(52) U.S. Cl.
CPC . *A61M 1/30* (2013.01); *A61M 1/16* (2013.01); *A61M 1/1613* (2014.02); *A61M 1/3609* (2014.02)

(58) Field of Classification Search
CPC .................... A61M 1/14; A61M 1/16–1/1619; A61M 1/282; A61M 1/34–1/341; A61M 1/385
USPC ............................................... 604/4.01–6.16
See application file for complete search history.

(56) References Cited

U.S. PATENT DOCUMENTS

2006/0116624 A1 6/2006 Sternby
2009/0024078 A1* 1/2009 Abe et al. ...................... 604/43
(Continued)

FOREIGN PATENT DOCUMENTS

EP 1698340 9/2006
JP 2007-029705 2/2007
(Continued)

OTHER PUBLICATIONS

European Search Report for Euopean Application No. 11806874.1, mail date is Nov. 21, 2014.
(Continued)

*Primary Examiner* — Philip R Wiest
*Assistant Examiner* — Benjamin Klein
(74) *Attorney, Agent, or Firm* — Greenblum & Bernstein, P.L.C.

(57) ABSTRACT

A hemodialysis system includes a body fluid volume calculating unit, a dialysis condition input unit with which blood flow velocity and dialysis fluid flow velocity in hemodialysis treatment performed after specific hemodialysis treatment can be input and input values of the blood flow velocity and the dialysis fluid flow velocity can be adjusted, a dialysis dose calculating unit configured to calculate, when the blood flow velocity and the dialysis fluid flow velocity are input to the dialysis condition input unit, by analyzing a mathematical model concerning urea kinetics, a dialysis dose of the hemodialysis treatment from the input blood flow velocity and the input dialysis fluid flow velocity, a body fluid volume calculated by the body fluid volume calculating unit, and the like, and a dialysis dose display unit configured to display the hemodialysis dose calculated by the dialysis dose calculating unit.

18 Claims, 14 Drawing Sheets

(56) References Cited

U.S. PATENT DOCUMENTS

2009/0221948 A1* 9/2009 Szamosfalvi et al. ....... 604/6.07
2012/0029324 A1* 2/2012 Akonur et al. ................ 600/309

FOREIGN PATENT DOCUMENTS

WO 2004/039436 5/2004
WO 2007/140993 12/2007

OTHER PUBLICATIONS

Takahiro Shinzato et al., "Method of calculating the dialysis fluid flow rate at which the targeted value of Kt/V is attained", Journal of Japanese Society for Dialysis Therapy, 2009, 42, pp. 921-929.

* cited by examiner

HEMODIALYSIS SYSTEM

TECHNICAL FIELD

The present invention relates to a hemodialysis system.

BACKGROUND ART

A dialysis dose is defined as a therapeutic dose of one hemodialysis treatment applied to a patient. As indexes of the dialysis dose, there are two indexes, i.e., a urea removal rate (R) and a Kt/V (=f(R)) value. In general, the Kt/V value is adopted. The Kt/V value of hemodialysis treatment is conventionally calculated by substituting, in a predetermined formula, serum urea concentrations measured at the start and at the end of hemodialysis treatment, a water removal volume during the hemodialysis treatment, and a treatment time of the hemodialysis treatment after completion of the hemodialysis treatment.

The serum urea concentration at the end of the hemodialysis treatment for calculating the Kt/V value can be determined by six factors, i.e., a body fluid volume, which is a total volume of water in the body of the patient, a hemodialysis treatment time, a water removal volume during the hemodialysis treatment, a mass-transfer area coefficient (in general, referred to as "$K_0A$"), which is an index indicating the performance of a dialyzer in use, blood flow velocity, and dialysis fluid flow velocity.

Incidentally, at present, a Kt/V value for minimizing a death rate, a so-called optimum Kt/V value, has been clarified by a large number of statistical surveys and researches. In hemodialysis treatment, it is necessary to execute hemodialysis treatment with which the optimum Kt/V value clarified by the large number of statistical surveys and researches can be attained. Therefore, usually, a medical staff member adjusts at least the blood flow velocity or the dialysis fluid flow velocity as an adjustment factor at the start of the hemodialysis treatment to thereby resultantly adjust the Kt/V value through adjustment of the serum urea concentration at the end of the hemodialysis treatment.

More specifically, at present, a hemodialysis facility first sets the optimum Kt/V value as a target Kt/V value. Then, the hemodialysis facility substitutes, in a predetermined formula, measured serum urea concentrations at the start and at the end of hemodialysis treatment in the past, a water removal volume during the same hemodialysis treatment, and a treatment time of the same hemodialysis treatment to calculate a Kt/V value of the hemodialysis treatment in the past. Then, after comparing the Kt/V value in the hemodialysis treatment in the past and the target Kt/V value, the hemodialysis facility adjusts, through trial and error, blood flow velocity or dialysis fluid flow velocity in hemodialysis treatment to be carried out while referring to blood flow velocity or dialysis fluid flow velocity in the hemodialysis treatment in the past such that a Kt/V value of the hemodialysis treatment to be carried out reaches the target Kt/V value.

The adjustment of the blood flow velocity and the dialysis fluid flow velocity is performed on the basis of a prediction through data of hemodialysis treatment in the past, empirical rules, and the like as explained above. Therefore, in reality, it is difficult to accurately attain the target Kt/V value as the Kt/V value of the hemodialysis treatment. Further, for example, the water removal volume, which is the factor for determining serum urea concentration at the end of the hemodialysis treatment and is used for calculation of the Kt/V value, changes in each hemodialysis treatment. A relation between the blood flow velocity and the Kt/V value in the hemodialysis treatment also changes for each patient and according to a dialyzer in use. Moreover, values of the other factors affecting the Kt/V value unpredictably change in this way. Therefore, even if the blood flow velocity and the dialysis fluid flow velocity are adjusted according to the data in the past and the like as explained above, it is difficult to accurately attain the target Kt/V value after the end of the hemodialysis treatment.

As a method for solving this problem, a method has been developed for calculating, by analyzing a mathematical model concerning urea kinetics, a body fluid volume, which is a total volume of water in a body of a patient, from measured serum urea concentration at the start of specific hemodialysis treatment and measured serum urea concentration at the end of the hemodialysis treatment, a dialysis treatment time of the hemodialysis treatment, a water removal volume during the hemodialysis treatment, blood flow velocity in the hemodialysis treatment, dialysis fluid flow velocity in the hemodialysis treatment and a mass-transfer area coefficient of a dialyzer used in the hemodialysis treatment during specific hemodialysis treatment and then during the hemodialysis treatment carried out after the specific hemodialysis treatment, kinetics dialysis fluid flow velocity necessary for attaining the target Kt/V value from the body fluid volume which had been calculated during the specific hemodialysis treatment and a planned dialysis treatment time, a planned water removal volume, blood flow velocity, a mass-transfer area coefficient of a dialyzer in use and the target Kt/V (Non-Patent Literature 1). According to this method, it is possible to more surely calculate dialysis fluid flow velocity for attaining the target Kt/V value for hemodialysis treatment to be performed.

CITATION LIST

Non-Patent Literature

Non-Patent Literature 1: Takahiro Shinzato, et al. "Calculation Method for a Dialysis Fluid Flow Rate at which a Target Kt/V Value is Obtained," Academic Journal of the Japanese Society for Dialysis Therapy 42, pp. 921 to 929, 2009

SUMMARY OF INVENTION

Technical Problem

However, when the dialysis fluid flow velocity necessary for attaining the target Kt/V value is calculated from the measured body fluid volume, the planned blood flow velocity, the target Kt/V, and the like as explained above, the calculated dialysis fluid flow velocity sometimes deviates from an allowable range in a hemodialysis system in which dialysis fluid flow velocity can be set. For example, in general, an upper limit of a setting value of dialysis fluid flow velocity in a hemodialysis system in wide general use is 700 mL/minute and a lower limit of the setting value is 300 mL/minute. These limits are set taking into account a range in which accuracy of dialysis fluid flow velocity in a dialysis fluid pump in use can be secured, costs of dialysis treatment due to a used volume of the dialysis fluid, and the like.

When the calculated dialysis fluid flow velocity deviates from the allowable range, it is necessary to set new blood flow velocity and/or a new target Kt/V value taking into account an allowable range of blood flow velocity and/or an allowable range of a target Kt/V value If the dialysis fluid flow velocity calculated by the recalculation deviates from the allowable range again, it is necessary to set blood flow velocity and/or a target Kt/V value for the third time and recalculate dialysis fluid flow velocity. In this way, it is necessary to repeat the recalculation until dialysis fluid flow velocity fits within the allowable range.

In such a case, operation for setting dialysis fluid flow velocity is complicated and time-consuming. Moreover, such operation is an extremely large burden for medical staff members who have to perform many kinds of operation such as measurement of blood pressure of a patient at a bed side at the start of dialysis and insertion of a dialysis puncture needle into a blood vessel.

On the other hand, in the method of Non-Patent Literature 1, it is also possible to change a target to be calculated from the dialysis fluid flow velocity to blood flow velocity and calculate the blood flow velocity from the body fluid volume, the target dialysis dose, the dialysis fluid flow velocity, and the like. However, concerning the blood flow velocity, there is also an allowable range defined from, for example, characteristics of a blood pump and it is necessary to fit the blood flow velocity within the range. Therefore, the same problem as the problem in calculating the dialysis fluid flow velocity occurs.

The present invention has been devised in view of such circumstances and it is an object of the present invention to easily and quickly perform, for hemodialysis treatment to be performed, setting of dialysis fluid flow velocity and/or blood flow velocity at which a target dialysis dose such as a target Kt/V value can be attained.

Solution to Problem

The present invention for attaining the object is a hemodialysis system including: a hemodialysis executing unit including a dialyzer configured to purify blood, a blood supply channel for supplying the blood extracted from a body to the dialyzer, a blood pump provided in the blood supply channel and for delivering the blood to the dialyzer, a blood return channel for returning the blood purified by the dialyzer to the body, a dialysis fluid supply channel for supplying dialysis fluid to the dialyzer, a dialysis fluid pump provided in the dialysis fluid supply channel and for supplying the dialysis fluid to the dialyzer, and a dialysis fluid discharge channel for discharging, from the dialyzer, the dialysis fluid used for purifying the blood in the dialyzer; a body fluid volume calculating unit configured to calculate, by analyzing a mathematical model concerning urea kinetics, a body fluid volume, which is a total volume of water in the body of a patient, from measured serum urea concentration at the start of first hemodialysis treatment and measured serum urea concentration at the end of the first hemodialysis treatment, a dialysis treatment time of the first hemodialysis treatment, a water removal volume in the first hemodialysis treatment, blood flow velocity in the first hemodialysis treatment, dialysis fluid flow velocity in the first hemodialysis treatment, and a mass-transfer area coefficient of the dialyzer used for the first hemodialysis treatment; a dialysis condition input unit with which blood flow velocity and dialysis fluid flow velocity in second hemodialysis treatment performed after the first hemodialysis treatment can be input and input values of the blood flow velocity and the dialysis fluid flow velocity can be adjusted; a dialysis dose calculating unit configured to calculate, when the blood flow velocity and the dialysis fluid flow velocity are input to the dialysis condition input unit, by analyzing the mathematical model concerning urea kinetics, a dialysis dose of the second hemodialysis treatment from the input blood flow velocity and the input dialysis fluid flow velocity, a mass-transfer area coefficient of the dialyzer used for the second hemodialysis treatment, a body fluid volume calculated by the body fluid volume calculating unit, a planned treatment time of the second hemodialysis treatment, and a planned water removal volume in the second hemodialysis treatment; and a dialysis dose display unit configured to display the hemodialysis dose calculated by the dialysis dose calculating unit.

In the hemodialysis system, the blood flow velocity and the dialysis fluid flow velocity can be input to the dialysis condition input unit while being caused to fluctuate stepwise, the dialysis dose calculating unit may calculate the dialysis dose at each of the steps of the blood flow velocity and the dialysis fluid flow velocity, and the dialysis dose display unit may display the dialysis dose at each of the steps.

At least an upper limit value or a lower limit value that can be input may be able to be set in the dialysis condition input unit concerning at least the blood flow velocity or the dialysis fluid flow velocity.

A range in which the blood flow velocity can be set may be set in a range in which set blood flow velocity set in the blood pump during the second hemodialysis treatment and actual blood flow velocity coincide with each other.

The upper limit value of the range in which the blood flow velocity can be input may be a value of the set blood flow velocity at the time when venous pressure of the blood return channel on a more downstream side than the dialyzer is measured while changing the set blood flow velocity of the blood pump and the venous pressure deviates from a regression line between the set blood flow velocity of the blood pump and the venous pressure.

The upper limit value of the range in which the blood flow velocity can be input may be a value of the set blood flow velocity at the time when arterial pressure of the blood supply channel on a more upstream side than the blood pump is measured while changing the set blood flow velocity of the blood pump and the arterial pressure deviates from a regression line between the set blood flow velocity of the blood pump and the arterial pressure.

The upper limit value of the range in which the blood flow velocity can be input may be an upper limit value of the blood flow velocity for not causing a jet stream in a vein-side puncture needle during the second hemodialysis treatment.

The hemodialysis system may further include an actual blood flow velocity calculating unit configured to calculate actual blood flow velocity, which is obtained when the blood flow velocity input in the dialysis condition input unit is set as set blood flow velocity, from a regression line between set blood flow velocity set in the blood pump during the second hemodialysis treatment and pressure of the blood supply channel or the blood return channel, and the dialysis dose calculating unit may calculate the dialysis dose using the actual blood flow velocity calculated by the actual blood flow velocity calculating unit.

The hemodialysis system including the dialysis condition input unit with which an upper limit value of the blood flow velocity can be set further includes a blood flow velocity upper limit value calculating unit configured to calculate an upper limit value of the blood flow velocity in the first hemodialysis treatment according to a method of at least (a) or (b), wherein the method (a) is a method of measuring, while changing set blood flow velocity of the blood pump, venous pressure of the blood return channel on a more downstream side than the dialyzer, calculating a value of the set blood flow velocity at the time when the venous pressure deviates from a regression line between the set blood flow velocity of the blood pump and the venous pressure, and setting the value of the set blood flow velocity as the upper limit value of the blood flow velocity, the method (b) is a method of measuring, while changing the set blood flow velocity of the blood pump, arterial pressure of the blood supply channel on a more upstream side than the blood pump, calculating a value of the set blood flow velocity at the time when the arterial pressure deviates from a regression line between the set blood flow velocity of the blood pump and the arterial pressure, and setting the value of the set blood flow velocity as the upper limit value of the blood flow velocity, and the upper limit value of the blood flow velocity calculated by the blood flow velocity upper limit value calculating unit is set in the dialysis condition input unit.

The blood flow velocity upper limit value calculating unit may set a smaller value of the values of the set blood flow velocity calculated by the methods (a) and (b) as the upper limit value of the blood flow velocity.

Advantageous Effect of Invention

According to the present invention, it is possible to easily and quickly perform setting of dialysis fluid flow velocity and blood flow velocity at which a target dialysis dose can be attained.

DESCRIPTION OF EMBODIMENT

Figure 1:
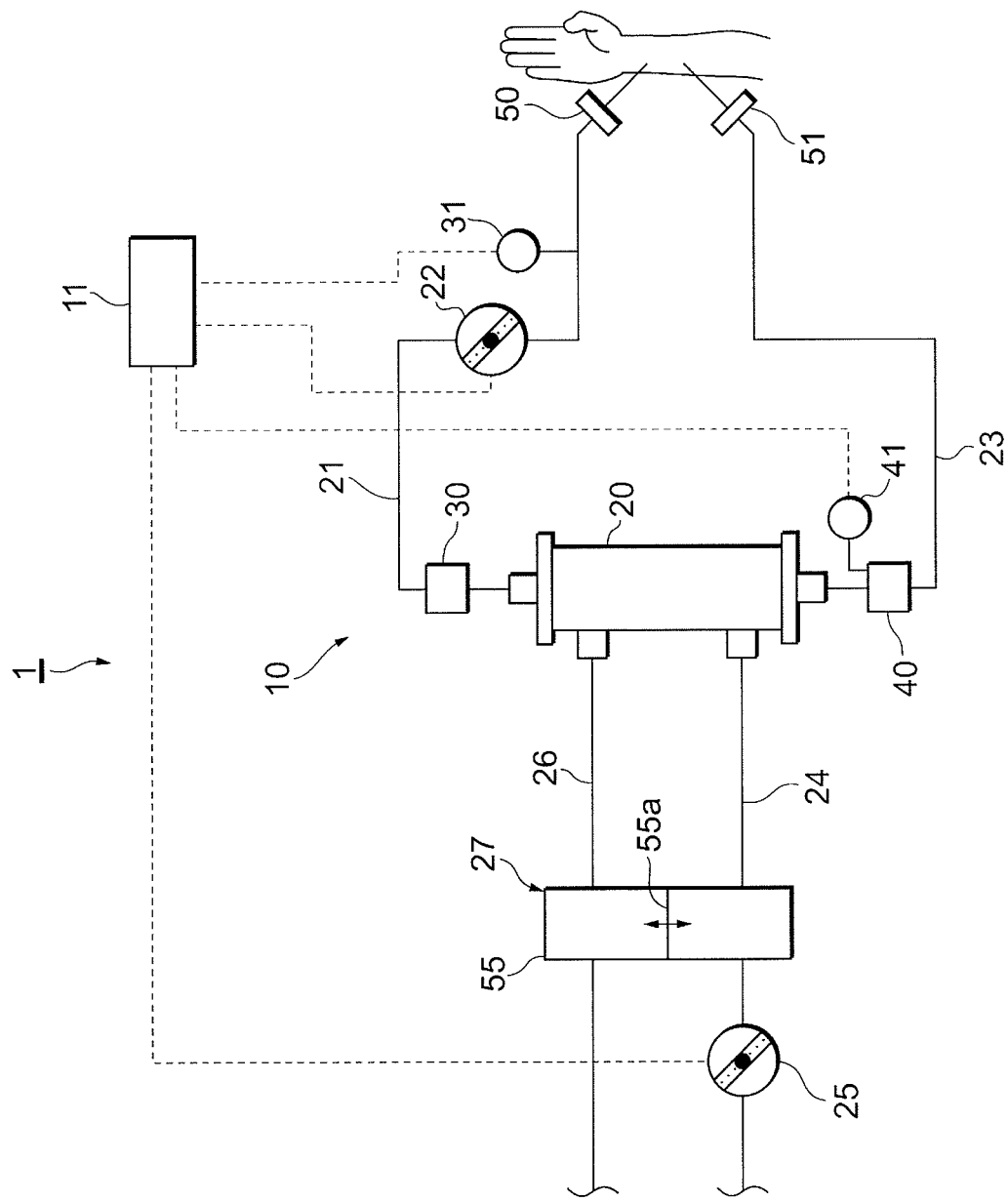
FIG. 1 is an explanatory diagram showing a schematic configuration of a hemodialysis system.

An example of an embodiment of the present invention is explained below with reference to the drawings. FIG. 1 is an explanatory diagram showing a schematic configuration of a hemodialysis system 1 according to this embodiment.

The hemodialysis system 1 includes, for example, a hemodialysis executing unit 10 and a control unit 11.

The hemodialysis executing unit 10 includes, for example, a dialyzer 20 configured to purify blood, a blood supply channel 21 for supplying the blood, which should be purified, extracted from a body to the dialyzer 20, a blood pump 22 provided on the blood supply channel 21 and for delivering the blood to the dialyzer 20, a blood return channel 23 connected to the dialyzer 20 and for returning the blood purified by the dialyzer 20 to the body, a dialysis fluid supply channel 24 connected to the dialyzer 20 and for supplying dialysis fluid to the dialyzer 20, a dialysis fluid pump 25 provided on the dialysis fluid supply channel 24 and for delivering the dialysis fluid to the dialyzer 20, a dialysis fluid discharge channel 26 for discharging, from the dialyzer 20, the dialysis fluid used to purify the blood in the dialyzer 20, and water removing means 27 driven such that a difference between a discharge volume per unit time of the dialyzer 20 and a delivery volume per unit time of the dialysis fluid to the dialyzer 20 is equalized with water removing speed from the body.

In the dialyzer 20, for example, a hollow fiber module is used. For example, the blood supply channel 21 and the blood return channel 23 are connected to a primary side of a hollow fiber membrane and the dialysis fluid supply channel 24 and the dialysis fluid discharge channel 26 are connected to a secondary side of the hollow fiber membrane.

The blood supply channel 21, the blood return channel 23, the dialysis fluid supply channel 24, and the dialysis fluid discharge channel 26 are formed by soft and elastic tubes. A drip chamber 30 and an artery-side pressure sensor 31 are provided in the blood supply channel 21. The artery-side pressure sensor 31 is provided on a more upstream side than the blood pump 22. A drip chamber 40 and a vein-side pressure sensor 41 are provided in the blood return channel 23. The vein-side pressure sensor 41 is provided in the drip chamber 40. An artery-side puncture needle 50 is connected to the distal end of the blood supply channel 21. A vein-side puncture needle 51 is connected to the distal end of the blood return channel 23.

As the blood pump 22 and the dialysis fluid pump 25, roller pumps are used. The blood and the dialysis fluid can be delivered by squeezing the soft tubes of the blood supply channel 21 and the dialysis fluid supply channel 24 using rotating rollers.

The water removing means 27 includes, for example, a container 55 including a displaceable partition wall 55a that partitions the inside having a fixed volume into two chambers and a branch channel (not shown) that branches from the dialysis fluid discharge channel 26. The container 55 can supply the dialysis fluid from one chamber to the dialyzer 20 through the dialysis fluid supply channel 24 and return the dialysis fluid in the dialyzer 20 to the other chamber through the dialysis fluid discharge channel 26 according to the movement of the partition wall 55a. Since volume fluctuation of one chamber and volume fluctuation of the other chamber due to the movement of the partition wall 55a are equal, a volume of the dialysis fluid sent from the one chamber to the dialyzer 20 and a volume of fluid returned from the dialyzer 20 to the other chamber are equal. And the dialysis fluid volume equivalent to a water removal volume from the body in the dialyzer 20 is discharged through the branch channel. Therefore, according to the driving of the water removing means 27, a difference between a discharge volume per unit time of the dialysis fluid from the dialyzer 20 and a delivery volume per unit time of the dialysis fluid to the dialyzer 20 is equalized with water removing speed from the body in the dialyzer 20.

The control unit 11 includes, for example, a computer. The control unit 11 can control the operation of the blood pump 22, the dialysis fluid pump 25, the water removing means 27, and the like and execute hemodialysis by executing various programs stored in, for example, a memory. The control unit 11 can execute, by executing a program, calculation of a body fluid volume, calculation of a target Kt/V value as a target dialysis dose, and the like explained below.

Figure 2:
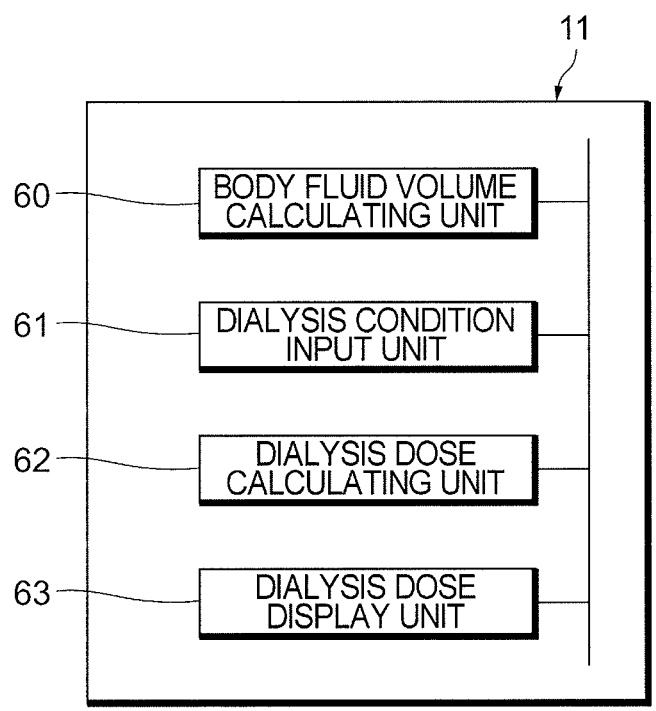
FIG. 2 is a block diagram showing the configuration of a control unit.

The control unit 11 includes, for example, as shown in FIG. 2, a body fluid volume calculating unit 60, a dialysis condition input unit 61, a dialysis dose calculating unit 62, and a dialysis dose display unit 63. The units 60 to 63 are electrically connected to one another and can communicate data.

Figure 3:
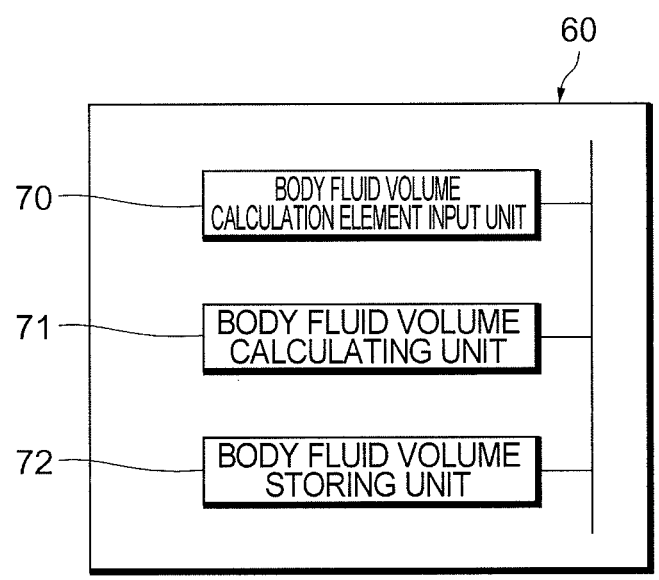
FIG. 3 is a block diagram showing the configuration of a body fluid volume calculating unit.

The body fluid volume calculating unit 60 includes, for example, as shown in FIG. 3, a body fluid volume calculation element input unit 70, a body fluid volume calculating unit 71, and a body fluid volume storing unit 72. The units 70 to 72 are electrically connected to one another and can communicate data.

For example, measured serum urea concentration at the start of specific hemodialysis treatment as first hemodialysis treatment, measured serum urea concentration at the end of the specific hemodialysis treatment, a dialysis treatment time of the specific hemodialysis treatment, a water removal volume of the specific hemodialysis treatment, blood flow velocity (driving speed of the blood pump 22) in the specific hemodialysis treatment, dialysis fluid flow velocity (driving speed of the dialysis fluid pump 25) in the specific hemodialysis treatment, and a mass-transfer area coefficient of urea of a dialyzer used for the specific hemodialysis treatment can be input to the body fluid volume calculation element input unit 70. The body fluid volume calculating unit 71 can calculate a body fluid volume, which is a total volume of water in the body of a patient, by analyzing a mathematical model concerning urea kinetics. The body fluid volume calculated by the body fluid volume calculating unit 71 is output to and stored in the body fluid volume storing unit 72. Note that the mathematical model concerning urea kinetics includes a plurality of factors related to one another with which the model can be analyzed. When a numerical value of one of the factors is unknown, the unknown factor can be derived from the other factors. Details are explained below.

Figure 4:
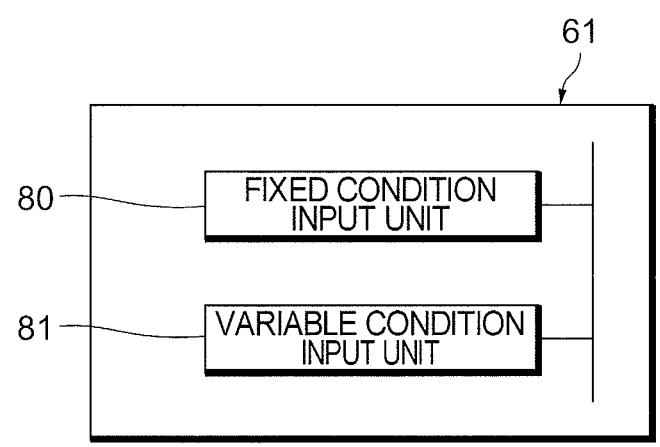
FIG. 4 is a block diagram showing the configuration of a dialysis condition input unit.

The dialysis condition input unit 61 includes, as shown in FIG. 4, a fixed condition input unit 80 and a variable condition input unit 81. A mass-transfer area coefficient of the dialyzer 20, the body fluid volume stored in the body fluid volume storing unit 72, a planned treatment time and a planned water removal volume can be automatically or manually input to the fixed condition input unit 80. Blood flow velocity and dialysis fluid flow velocity planned in the hemodialysis treatment as second hemodialysis treatment executed after the specific hemodialysis treatment in which the body fluid volume is calculated, can be input to the variable condition input unit 81. Input values of the blood flow velocity and the dialysis fluid flow velocity can be adjusted.

Figure 5:
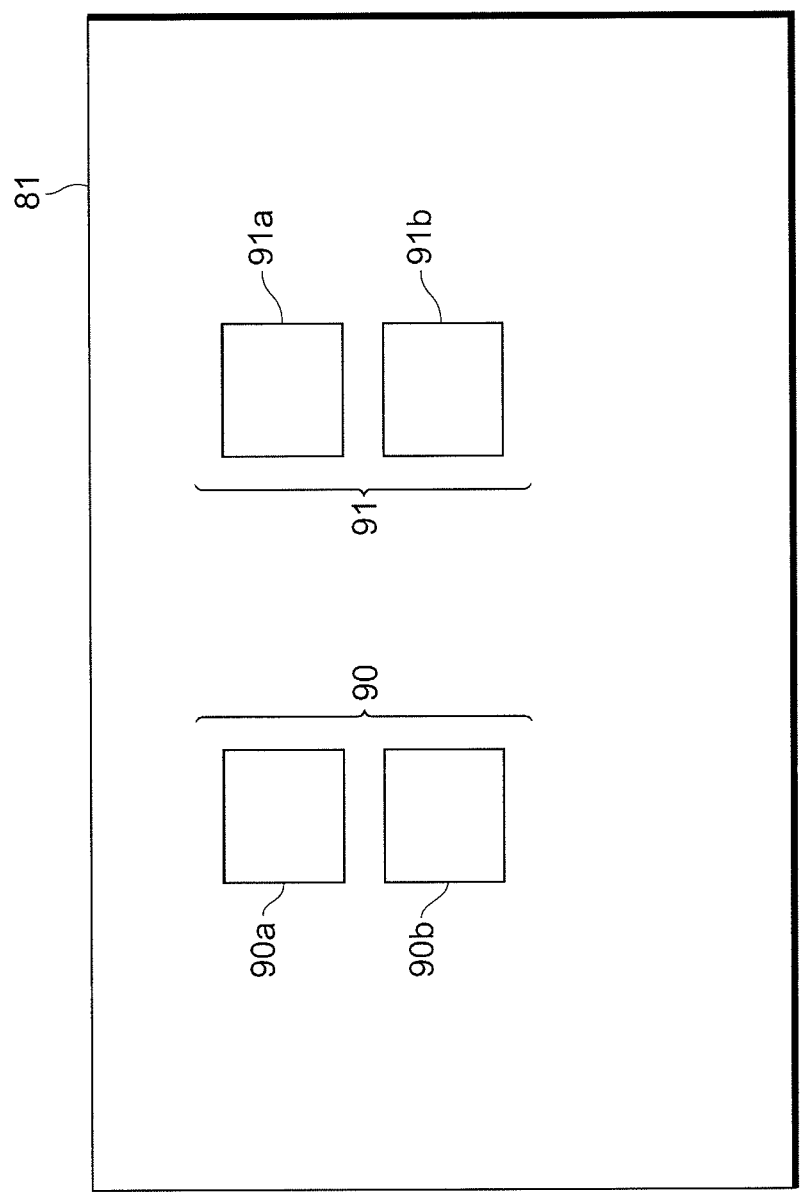
FIG. 5 is an explanatory diagram showing adjustment buttons of the dialysis condition input unit.

For example, as shown in FIG. 5, a blood flow velocity adjustment button 90 for inputting blood flow velocity and a dialysis fluid flow velocity adjustment button 91 for inputting dialysis fluid flow velocity are provided in the variable condition input unit 81. With the blood flow velocity adjustment button 90 and the dialysis fluid flow velocity adjustment button 91, it is possible to input blood flow velocity and dialysis fluid flow velocity while causing the blood flow velocity and the dialysis fluid flow velocity to fluctuate stepwise. For example, the blood flow velocity adjustment button 90 includes a blood flow velocity increase button 90a for increasing input blood flow velocity stepwise at a fixed interval while being pressed and a blood flow velocity reduction button 90b for reducing input blood flow velocity stepwise at a fixed interval while being pressed. Similarly, the dialysis fluid flow velocity adjustment button 91 includes a dialysis fluid flow velocity increase button 91a for increasing input dialysis fluid flow velocity stepwise at a fixed interval while being pressed and a dialysis fluid flow velocity reduction button 91b for reducing input dialysis fluid flow velocity stepwise at a fixed interval while being pressed. For example, blood flow velocity and dialysis fluid flow velocity input to the variable condition input unit 81 are displayed on a real time basis on the dialysis dose display unit 63 explained below.

When blood flow velocity and dialysis fluid flow velocity are input to the variable condition input unit 81 of the dialysis condition input unit 61, the dialysis dose calculating unit 62 acquires information concerning the input on a real time basis. The dialysis dose calculating unit 62 can calculate, by analyzing the mathematical model concerning urea kinetics, a Kt/V value of the hemodialysis treatment as second hemodialysis treatment executed after the specific hemodialysis treatment in which the body fluid volume is calculated from the acquired blood flow velocity, acquired dialysis fluid flow velocity, the mass-transfer area coefficient of the dialyzer 20 acquired from the fixed condition input unit 80, the body fluid volume calculated by the body fluid volume calculating unit 60, a planned treatment time of the hemodialysis treatment executed after the specific hemodialysis treatment in which the body fluid volume is calculated, and a planned water removal volume in the hemodialysis treatment executed after the specific hemodialysis treatment in which the body fluid volume is calculated. As explained above, when blood flow velocity and the dialysis fluid flow velocity are input to the variable condition input unit 81 stepwise, the dialysis dose calculating unit 62 can acquire the blood flow velocity and the dialysis fluid flow velocity at each of the steps and calculate a Kt/V value at each of the steps. Note that the mathematical model concerning urea kinetics includes a plurality of factors related to one another with which the model can be analyzed. When a numerical value of one of the factors is unknown, the unknown factor can be derived from the other factors. Details are explained below.

Figure 6:
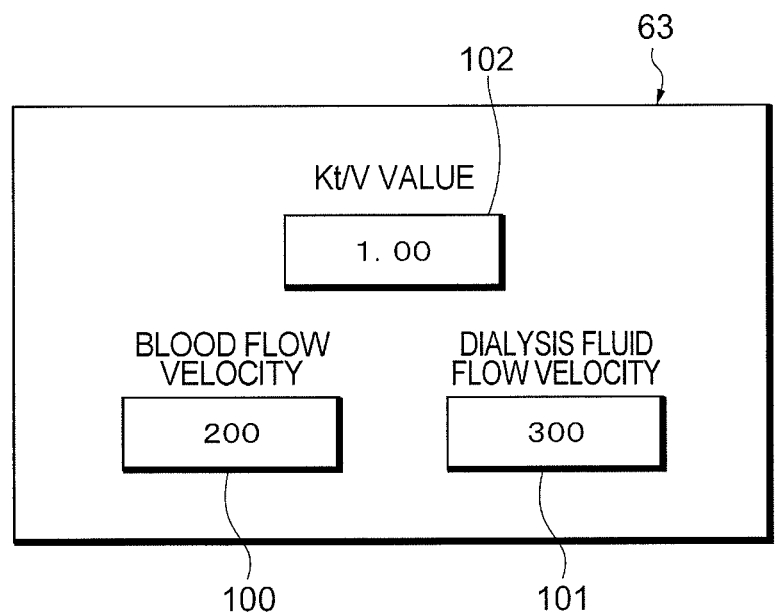
FIG. 6 is an explanatory diagram showing a dialysis dose display unit.

The dialysis dose display unit 63 includes, for example, as shown in FIG. 6, a blood flow velocity display screen 100 configured to display, on a real time basis, blood flow velocity input in the dialysis condition input unit 61, a dialysis fluid flow velocity display screen 101 configured to display dialysis fluid flow velocity on a real time basis, and a dialysis dose display screen 102 configured to display, on a real time basis, a Kt/V value calculated by the dialysis dose calculating unit 62.

An example of the operation of the hemodialysis system 1 configured as explained above is explained below. The operation is realized by, for example, executing the program of the control unit 11.

First, the body fluid volume calculating unit 60 calculates a body fluid volume of a patient for whom hemodialysis treatment is executed. The body fluid volume of the patient is calculated in the body fluid volume calculating unit 71, by analyzing the mathematical model of urea kinetics, from measured serum urea concentration at the start and end of specific hemodialysis treatment in a day of a regular blood sampling performed at a frequency of, for example, once in about one month, a dialysis treatment time of the specific hemodialysis treatment, a water removal volume during the specific hemodialysis treatment, blood flow velocity in the specific hemodialysis treatment, dialysis fluid flow velocity in the specific hemodialysis treatment, and a mass-transfer area coefficient of the dialyzer 20 used for the specific hemodialysis treatment, which are input from the body fluid volume calculation factor input unit 70. The calculated body fluid volume is output to and stored in the body fluid volume storing unit 72. Note that, usually, a body fluid volume of a dialysis patient does not substantially change at least for one month. Therefore, the body fluid volume of the patient calculated by the body fluid volume calculating unit 71 and stored in the body fluid volume storing unit 72 can be effectively used for at least one month until the next regular blood sampling is performed.

Next, in hemodialysis treatment executed for, for example, about one month after the specific hemodialysis treatment in which the body fluid volume is calculated, blood flow velocity and dialysis fluid flow velocity are input to the variable condition input unit 81 by the blood flow velocity adjustment button 90 and the dialysis fluid flow velocity adjustment button 91. Values of the blood flow velocity and the dialysis fluid flow velocity are displayed on the dialysis dose display unit 63 on a real time basis. The body fluid volume stored in the body fluid volume storing unit 72, a mass-transfer area coefficient of the dialyzer 20 used in the hemodialysis treatment, a planned treatment time of the hemodialysis treatment, and a planned water removal volume of the hemodialysis treatment are input to the fixed condition input unit 80.

When the blood flow velocity and the dialysis fluid flow velocity are input to the variable condition input unit 81, information concerning the input is immediately sent to the dialysis dose calculating unit 62. The dialysis dose calculating unit 62 calculates a Kt/V value. The Kt/V value is calculated, by analyzing the mathematical model concerning urea kinetics, from the blood flow velocity and the dialysis fluid flow velocity acquired from the variable condition input unit 81, the mass-transfer area coefficient of the dialyzer 20, the body fluid volume, the planned treatment time of the hemodialysis treatment, and the planned water removal volume in the hemodialysis treatment acquired from the fixed condition input unit 80.

As shown in FIG. 6, the calculated Kt/V value is immediately displayed on the dialysis dose display unit 63 together with the values of the blood flow velocity and the dialysis fluid flow velocity input to the variable condition input unit 81.

When the calculated Kt/V value, the input values of the blood flow velocity and the dialysis fluid flow velocity, a combination of the Kt/V value and the blood flow velocity and the dialysis fluid flow velocity, or the like is adjusted again, for example, the blood flow velocity adjustment button 90 or the dialysis fluid flow velocity adjustment button 91 of the variable condition input unit 81 is pressed and the values of the blood flow velocity and the dialysis fluid flow velocity are adjusted. For example, when the blood flow velocity is reduced, the blood flow velocity reduction button 90b is pressed. Blood flow velocity decreasing stepwise at an interval of, for example, 5 mL/minute is input to the dialysis condition input unit 61 while the blood flow velocity reduction button 90b is pressed. When the blood flow velocity is increased, the blood flow velocity increase button 90a is pressed. Blood flow velocity increasing stepwise at an interval of, for example, 5 mL/minute is input to the dialysis condition input unit 61 while the blood flow velocity increase button 90a is pressed. When the dialysis fluid flow velocity is reduced, the dialysis fluid flow velocity reduction button 91b is pressed. Dialysis fluid flow velocity decreasing stepwise at an interval of, for example, 10 mL/minute is input to the dialysis condition input unit 61 while the dialysis fluid flow velocity reduction button 91b is pressed. When the dialysis fluid flow velocity is increased, the dialysis fluid flow velocity increase button 91a is pressed. Dialysis fluid flow velocity increasing stepwise at an interval of, for example, 10 mL/minute is input to the dialysis condition input unit 61 while the dialysis fluid flow velocity increase button 91a is pressed. When new blood flow velocity or new dialysis fluid flow velocity is input stepwise in this way, the dialysis dose calculating unit 62 immediately calculates a Kt/V value at each of the steps of the blood flow velocity or the dialysis fluid flow velocity. The calculated Kt/V value is displayed on the dialysis dose display unit 63. At a point when a desired Kt/V value, desired values of blood flow velocity and dialysis fluid flow velocity, and the like are obtained, the blood flow velocity adjustment button 90 and the dialysis fluid flow velocity adjustment button 91 are stopped being pressed. When the medical staff member inputs and adjusts arbitrary blood flow velocity and dialysis fluid flow velocity in this way, a Kt/V value corresponding to the blood flow velocity and the dialysis fluid flow velocity is instantaneously calculated and displayed. Thereafter, the hemodialysis treatment is performed according to the new setting.

According to the embodiment explained above, when arbitrary blood flow velocity and dialysis fluid flow velocity are input and adjusted, a Kt/V value corresponding to the blood flow velocity and the dialysis fluid flow velocity is instantaneously calculated and displayed. Therefore, it is possible to easily and quickly perform, for the hemodialysis treatment executed after the specific hemodialysis treatment in which the body fluid volume is calculated, setting of dialysis fluid flow velocity and blood flow velocity at which a target Kt/V value can be attained.

The blood flow velocity and the dialysis fluid flow velocity can be input to the dialysis condition input unit 61 while being caused to fluctuate stepwise. The dialysis dose calculating unit 62 calculates a dialysis dose at each of the steps of the blood flow velocity and the dialysis fluid flow velocity. The dialysis dose display unit 63 displays the dialysis dose at each of the steps. Therefore, for example, it is possible to more quickly perform setting of dialysis fluid flow velocity and blood flow velocity at which a target Kt/V value can be attained. Since the dialysis dose is displayed at each of the steps, it is possible to increase or reduce the blood flow velocity and the like while looking at the dialysis dose. It is easy to find and set appropriate blood flow velocity and the like.

In the dialysis condition input unit 61 described in the embodiment, upper limit values and lower limit values of the blood flow velocity and the dialysis fluid flow velocity may be able to be set. In such a case, for example, in the dialysis condition input unit 61, ranges in which blood flow velocity and dialysis fluid flow velocity can be input are set. The ranges of the blood flow velocity and the dialysis fluid flow velocity are decided from, for example, a viewpoint of conditions peculiar to the hemodialysis system 1 and the like. Specifically, the range of the blood flow velocity is decided from a viewpoint of a blood access condition, blood status, a puncture state, and the like of a patient. The range of the dialysis fluid flow velocity is decided from a viewpoint of a range in which the accuracy of the dialysis fluid pump 25 can be secured in the hemodialysis system 1 or a viewpoint of costs of hemodialysis treatment (a reduction in an amount of use of expensive dialysis fluid) or the like. Consequently, even if the adjustment buttons 90 and 91 of the dialysis condition input unit 61 continue to be pressed, the values of the blood flow velocity and the dialysis fluid flow velocity stop fluctuating when the values exceed the ranges in which the blood flow velocity and the dialysis fluid flow velocity can be input. Consequently, input of values of blood flow velocity and dialysis fluid flow velocity at which hemodialysis treatment cannot be realistically carried out is prevented, hemodialysis treatment is properly performed, and the medical staff members can easily input blood flow velocity and dialysis fluid flow velocity. Note that the limitation of input values to the dialysis condition input unit 61 may be applied to only blood flow velocity or may be applied to only dialysis fluid flow velocity according to performances of the hemodialysis systems 1. Only the upper limit values or the lower limit values may be set concerning the limitation of input values of blood flow velocity and dialysis fluid flow velocity.

In the example explained above, for example, when the limitation of an input value of blood flow velocity is applied, a range in which blood flow velocity can be input may be set to a range in which the blood flow velocity set in the blood pump 22 and the actual blood flow velocity coincide with each other during hemodialysis treatment.

Figure 7:
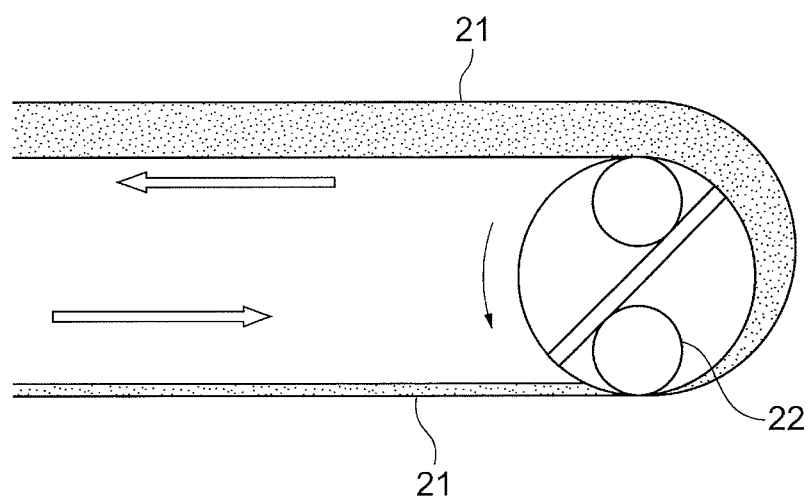
FIG. 7 is an explanatory diagram showing a state in which blood in a blood supply channel is sent by a blood pump and the blood supply channel on an upstream side is narrowed.

For example, when blood flow velocity input from the dialysis condition input unit 61, (i.e., blood flow velocity set in the blood pump 22) exceeds a certain level, velocity of a blood flow actually delivered by the blood pump is lower than the set blood flow velocity. This is caused by a characteristic of the blood pump, which is a so-called roller pump. Specifically, as shown in FIG. 7, in the blood pump 22, which is the roller pump, the roller crushes and squeezes the elastic blood supply channel 21 to thereby deliver blood. The crushed blood supply channel 21 returns to the original shape with a restoring force of the channel itself and the pressure of the blood supply channel 21 on the upstream side of the blood pump 22. At that point, the blood supply channel 21 is filled with blood again. However, when a setting value of blood flow velocity of the blood pump 22 is too high and the blood supply channel 21 is squeezed too strongly by the roller, the pressure of the blood supply channel 21 on the upstream side of the blood pump 22 decreases and the blood supply channel 21 does not sufficiently return to the original shape. As a result, actual blood flow velocity is lower than the set value of the blood flow velocity of the blood pump 22 and a difference occurs between the set value and the actual blood flow velocity. When too high blood flow velocity of the blood pump 22 is set, the same blood flow velocity as the set blood flow velocity is not actually obtained. Therefore, a Kt/V value calculated by inputting blood flow velocity set in the blood pump 22 lacks accuracy. As a result, even if hemodialysis treatment is performed in such setting, a target Kt/V value cannot be attained.

On the other hand, a more accurate Kt/V value is calculated by setting the range in which blood flow velocity can be input to a range in which the set blood flow velocity and actual blood flow velocity of the blood pump 22 coincide with each other.

Figure 8:
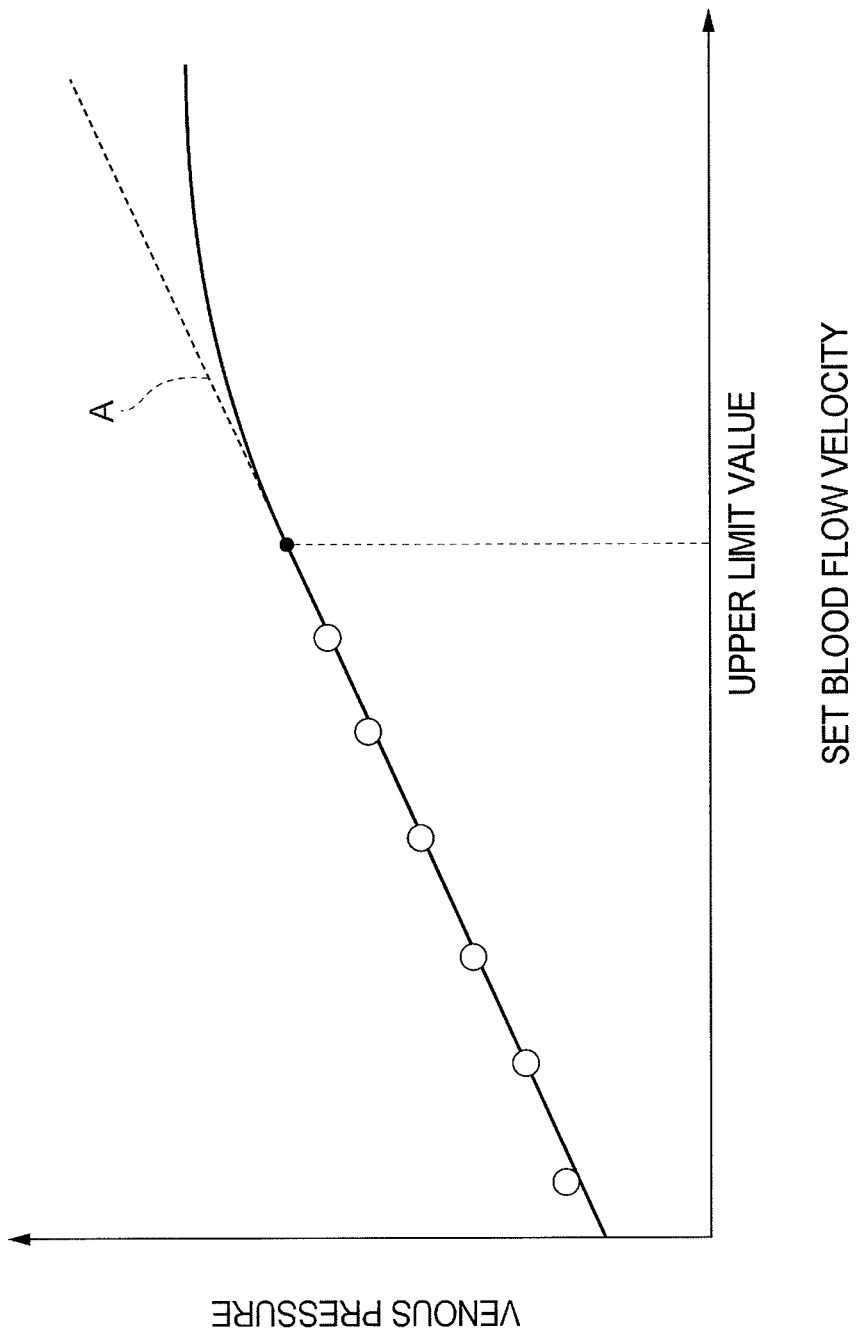
FIG. 8 is a graph showing a regression line between set blood flow velocity of the blood pump and venous pressure.

Further, when the range in which blood flow velocity can be input is set, it is also possible to measure internal pressure (venous pressure) of the blood return channel 23 on a more downstream side than the dialyzer 20 while increasing the set blood flow velocity of the blood pump 22 stepwise and set, as an upper limit value of the range in which blood flow velocity can be input, a value of set blood flow velocity at the time when the venous pressure deviates from a regression line A between the set blood flow velocity of the blood pump 22 and the venous pressure as shown in FIG. 8.

For example, venous pressure of the drip chamber 40 and an actual blood flow velocity are in a linear relation (a proportionality relation). Therefore, as long as the set blood flow velocity of the blood pump 22 and actual blood discharge velocity (blood flow velocity) coincide with each other, as shown in FIG. 8, the set blood flow velocity of the blood pump 22 and the venous pressure are in a linear relation. When the set blood flow velocity of the blood pump 22 exceeds a certain level and actual blood flow velocity by the blood pump 22 is lower than the set blood flow velocity, the venous pressure deviates from the regression line A between the venous pressure and the set blood flow velocity of the blood pump 22. The venous pressure is lower than that on the regression line A which corresponds to the set blood flow velocity. This is considered to be because, as shown in FIG. 7, when the set blood flow velocity of the blood pump 22 is too high, the roller squeezes the tube of the blood supply channel 21 too strongly, and the pressure of the blood supply channel 21 on the upstream side of the blood pump 22 is too low compared to a certain level, the blood supply channel 21 is crushed and does not sufficiently return to the original shape and the blood pump 22 is in a so-called idling state, and as a result, even if the set blood flow velocity is further increased, an increase in the venous pressure is gentler. Making use of this phenomenon, while the set blood flow velocity of the blood pump 22 is increased stepwise, venous pressure is measured by the venous side pressure sensor 41. Then, a value of the set blood flow velocity at the time when the venous pressure deviates from the regression line A between the set blood flow velocity of the blood pump 22 and the venous pressure is set as an upper limit of the range in which blood flow velocity can be input.

The pressure (venous pressure) of the blood return channel 23 on the more downstream side than the dialyzer 20 is affected by the inner diameter of the venous-side puncture needle 51 in use, the internal pressure of the access blood vessel of the patient, and the like. Therefore, it is difficult to predict a range in which the set blood flow velocity and actual blood flow velocity of the blood pump 22 coincide with each other. The range is different for each patient. Therefore, venous pressure is actually measured and an upper limit value of blood flow velocity is detected as explained above, whereby it is possible to accurately define the range in which blood flow velocity can be input.

Figure 9:
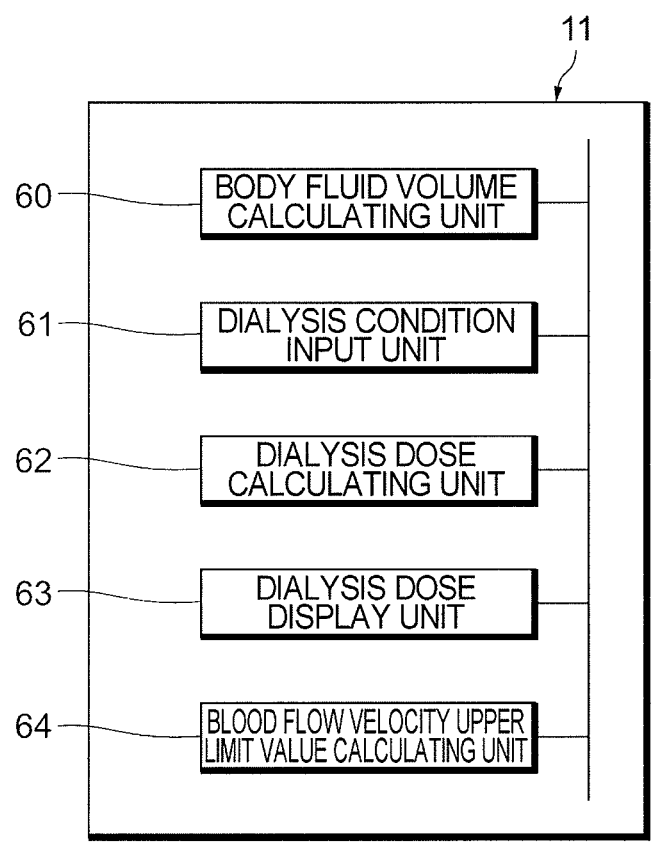
FIG. 9 is a block diagram showing the configuration of the control unit including a blood flow velocity upper limit value calculating unit.

Note that, as shown in FIG. 9, the upper limit value of the blood flow velocity may be calculated by a blood flow velocity upper limit value calculating unit 64 included in the control device 11. For example, in the first hemodialysis treatment, in the blood flow velocity upper limit value calculating unit 64, venous pressure of the blood return channel 23 on the more downstream side than the dialyzer 20 using is measured by the venous-side pressure sensor 41 at each value of the set blood flow velocity, while changing the set blood flow velocity of the blood pump 22. And the value of the set blood flow velocity at the time when the venous pressure deviates from the regression line A between the set blood flow velocity of the blood pump 22 and the venous pressure, is regarded as the upper limit of the blood flow velocity (a calculation method (a)). The upper limit value of the blood flow velocity calculated by the blood flow velocity upper limit value calculating unit 64 is set in the dialysis condition input unit 61. In such a case, setting of the upper limit value of the blood flow velocity can be automatically performed. When the venous pressure is measured at various set blood flow velocity, it is desirable to measure the venous pressure at 50 ml/min interval of the set blood flow velocity. It is more desirable to measure it at 10 ml/min interval of the set blood flow velocity. It is still more desirable to measure it at 5 ml/min interval of the set blood flow velocity. As the width of a plot of measurement data is narrower, accuracy of the calculation of the upper limit value is higher. When the upper limit value is calculated, the upper limit value can also be set as explained below. The regression line between the venous pressures and values of blood flow velocity is calculated. When the venous pressure deviates to lower pressure side from the regression line A at a higher values of blood flow velocity(see FIG. 8), the set blood flow velocity corresponding to the venous pressure deviating most slightly from the regression line A is regarded as the upper limit value of the set blood flow velocity. In this case, it is possible to select the set blood flow velocity corresponding to the venous pressure deviating most slightly from the regression line A.

Figure 10:
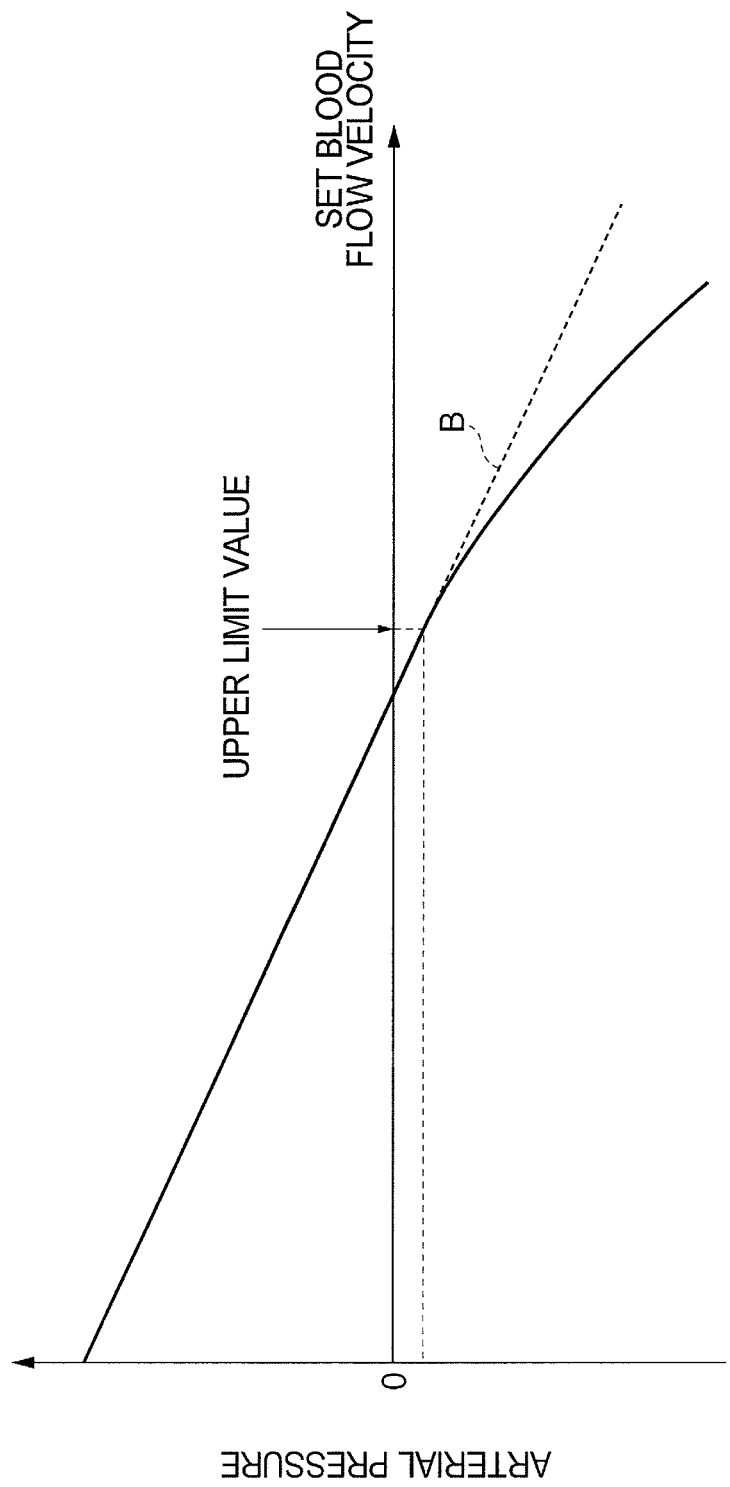
FIG. 10 is a graph showing a regression line between the set blood flow velocity of the blood pump and arterial pressure.

As another example, when the range in which blood flow velocity can be input is set, it is also possible to measure, while increasing the set blood flow velocity of the blood pump 22 stepwise, internal pressure (arterial pressure) of the blood supply channel 21 on the more upstream side than the blood pump 22 and set, as the upper limit value of the range in which blood flow velocity can be input, a value of the set blood flow velocity at which the arterial pressure begins to deviate from a regression line B between the set blood flow velocity of the blood pump 22 and the arterial pressure as shown in FIG. 10.

The arterial pressure on the more upstream side than the blood pump 22 and an actual blood flow volume are in a negative linear relation. Therefore, as long as the set blood flow velocity and actual blood flow velocity of the blood pump 22 coincide with each other, as shown in FIG. 10, the set blood flow velocity of the blood pump 22 and the arterial pressure are in a linear relation. When the set blood flow velocity of the blood pump 22 exceeds a certain level, the actual blood flow velocity of the blood pump 22 is lower than the set blood flow velocity. The arterial pressure deviates from the regression line B between the set blood flow velocity of the blood pump 22 and the arterial pressure and is lower than the regression line B. This is because, as shown in FIG. 7, when the set blood flow velocity of the blood pump 22 is too high, the roller squeezes the tube of the blood supply channel 21 too strongly, and the pressure of the blood supply channel 21 on the upstream side of the blood pump 22 is lower than a certain level, the blood supply channel 21 is crushed and does not return to the original shape and the blood pump 22 is in a so-called idling state, and as a result, even if the set blood flow velocity is further increased, the actual blood flow velocity does not increase as high as the set blood flow velocity. Making use of this phenomenon, while the set blood flow velocity of the blood pump 22 is increased stepwise, arterial pressure is measured by the artery-side pressure sensor 31 and a value of the set blood flow velocity at which the arterial pressure begins to deviate from the regression line B between the set blood flow velocity of the blood pump 22 and the arterial pressure is set as an upper limit of the range in which blood flow velocity can be input. In this example, as in the example explained above, since arterial pressure is actually measured and an upper limit value of blood flow velocity is detected, it is possible to more accurately define the range in which blood flow velocity can be input.

Note that the calculation of the upper limit value of the blood flow velocity may be performed by the blood flow velocity upper limit value calculating unit 64 of the control device 11. In the first hemodialysis treatment, the blood flow velocity upper limit value calculating unit 64 may measure, while changing the set blood flow velocity of the blood pump 22, arterial pressure of the blood supply channel 21 on the more upstream side than the blood pump 22, calculate a value of the set blood flow velocity at the time when the arterial pressure deviates from the regression line B between the set blood flow velocity of the blood pump 20 and the arterial pressure, and set the value of the set blood flow velocity as the upper limit of the blood flow velocity (a calculation method (b)). In the dialysis condition input unit 61, the upper limit value of the blood flow velocity calculated in the blood flow velocity upper limit value calculating unit 64 is set. In such a case, as in the case explained above, it is possible to automatically perform setting of the upper limit value of the blood flow velocity.

The blood flow velocity upper limit value calculating unit 64 may calculate, using the calculation method (a) and the calculation method (b), both of a value of the set blood flow velocity at the time when the venous pressure deviates from the regression line A between the set blood flow velocity of the blood pump 22 and the venous pressure and a value of the set blood flow velocity at the time when the arterial pressure deviates from the regression line B between the set blood flow velocity of the blood pump 20 and the arterial pressure and set a smaller value of the values of the set blood flow velocity as the upper limit value of the blood flow velocity. Consequently, it is possible to more appropriately set a range in which blood flow velocity can be input.

Incidentally, the blood purified by the dialyzer 20 passes through the blood return channel 23 to be returned into the blood access vessel through the puncture needle for vein 51. At this point, since the inner diameter of the puncture needle for vein 51 is far smaller than the inner diameter of the blood return channel 23, linear velocity of the blood returned into the blood access vessel increases in the puncture needle for vein 51 and the blood is jetted into the blood access vessel as a jet stream to sometimes hit the wall of the blood access vessel. This phenomenon in which the jet stream of the blood hits the blood access vessel wall is repeated for a long period in each dialysis treatment. The speed of the jet stream is higher as the puncture needle for vein 51 is thinner and a blood flow volume is larger. It is considered that the phenomenon in which the jet stream hits the blood access vessel wall is, in a long term, is one of the causes of stenosis of the blood access vessel and a frequency of stenosis of the blood access vessel is affected by strength of the jet stream hitting the blood access vessel wall. Empirically, when the puncture needle for vein 51 having thickness of 17 G is used, if blood flow velocity is equal to or lower than 300 mL/minute, a risk of stenosis of the blood access vessel decreases.

Therefore, an upper limit value of the blood flow velocity that can be input may be an upper limit value of blood flow velocity for not causing a jet stream in the puncture needle for vein 51 during hemodialysis treatment. Such an upper limit value of the blood flow velocity is set on the basis of, for example, the diameter of the venous-side puncture needle 51 and the diameter of the blood return channel 23 used in the hemodialysis treatment. It is also possible to measure venous pressure on the more downstream side than the dialyzer 20 while changing the set blood flow velocity of the blood pump 22 stepwise and set an upper limit of blood flow velocity, at which a jet stream does not occur, as such an upper limit value on the basis of a correlation between the set blood flow velocity of the blood pump 22 and the venous pressure detected by the measurement.

Consequently, a jet stream is prevented from occurring in the venous-side puncture needle 51. Consequently, for example, the jet stream does not hit the blood access vessel wall, stenosis and the like of the blood access vessel in a long term due to the jet stream can be prevented, and damage of blood access vessel wall due to the jet stream can be prevented.

It is also possible to compare an upper limit value of blood flow velocity in a range in which the set blood flow velocity and actual blood flow velocity of the blood pump 22 do not coincide with each other and an upper limit value of blood flow velocity for not causing a jet stream, so as to set a lower one of the upper limit values as the upper limit value that can be input. A lower limit value of blood flow velocity that can be input may be set to a lower limit value of blood flow velocity at which blood clotting does not occur during dialysis treatment or blood flow velocity at which a distribution of a blood flow in the dialyzer 20 is stable, for example, about 100 mL/minute.

In the embodiment, the dialysis dose calculating unit 62 calculates the Kt/V value directly using the blood flow velocity input to the dialysis condition input unit 61 and set in the blood pump 22 during hemodialysis treatment. However, the dialysis dose calculating unit 62 may calculate actual blood flow velocity from a regression line between the set blood flow velocity of the blood pump 22 and the pressure of the blood supply channel 21 or the blood return channel 23, when blood flow velocity input in the dialysis condition input unit 61 is set as the set blood flow velocity. It is possible to calculate a Kt/V value using the actual blood flow velocity calculated in this way.

Figure 11:
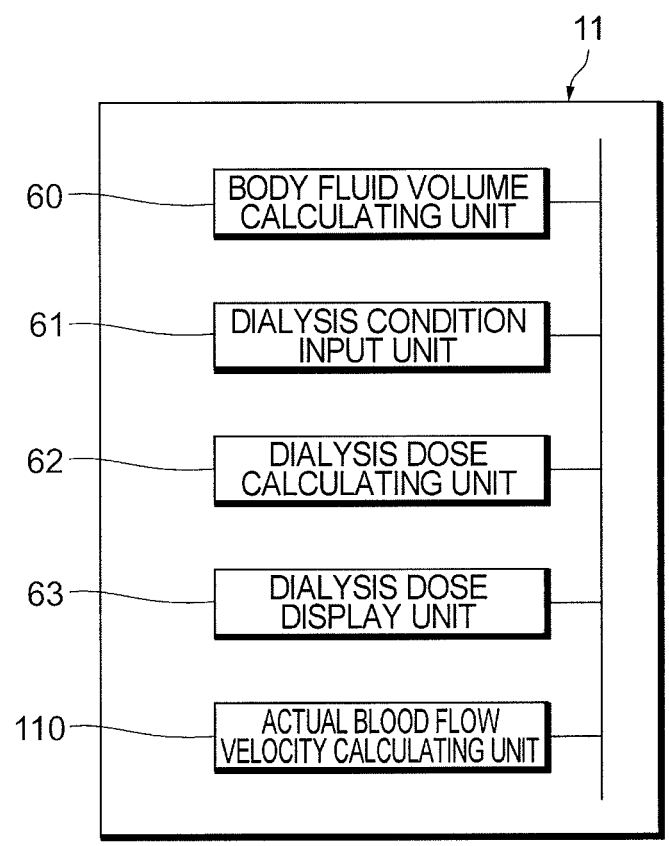
FIG. 11 is a block diagram showing the configuration of the control unit including an actual blood flow velocity calculating unit.
Figure 12:
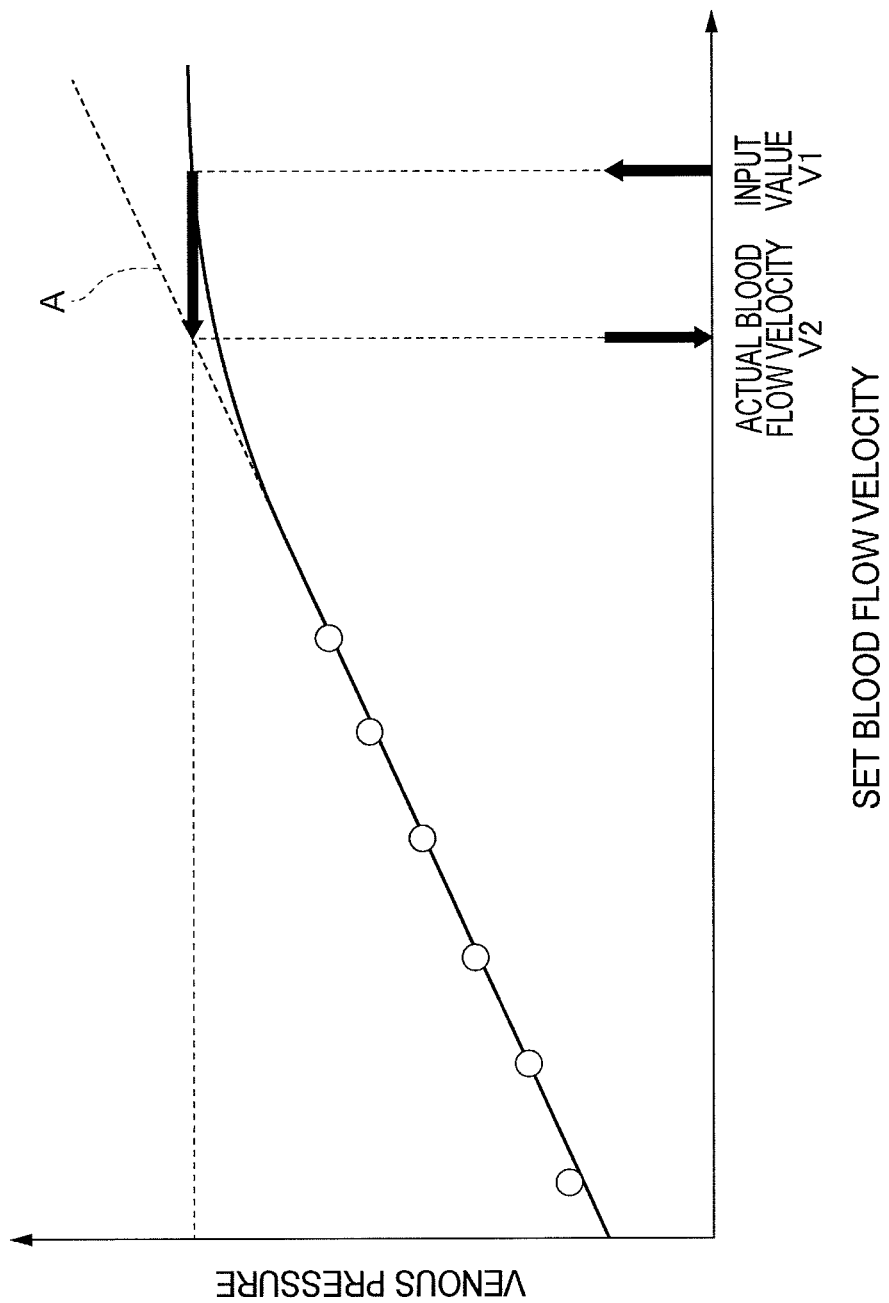
FIG. 12 is a graph showing actual blood flow velocity in the regression line between the set blood flow velocity of the blood pump and the venous pressure.

In such a case, for example, as shown in FIG. 11, an actual blood flow velocity calculating unit 110 is provided in the control unit 11. The actual blood flow velocity calculating unit 110 can calculate actual blood flow velocity from the regression line A between set blood flow velocity set in the blood pump 22 and venous pressure of the blood return channel 23 on the more downstream side than the dialyzer 20 shown in FIG. 12, when blood flow velocity input in the dialysis condition input unit 61 is set as the set blood flow velocity. For example, when the input blood flow velocity is set blood flow velocity V1, a value of set blood flow velocity on the regression line A of the venous pressure corresponding to the set blood flow velocity V1 is actual blood flow velocity V2.

When blood flow velocity and dialysis fluid flow velocity are input to the variable condition input unit 81 of the dialysis condition input unit 61, the dialysis dose calculating unit 62 can calculate, by analyzing the mathematical model concerning urea kinetics, a Kt/V value of hemodialysis treatment from the input dialysis fluid flow velocity, actual blood flow velocity calculated by the actual blood flow velocity calculating unit 110, a mass-transfer area coefficient of the dialyzer 20 used for the hemodialysis treatment input from the fixed condition input unit 80, a body fluid volume calculated by the body fluid volume calculating unit 60, a planned treatment time of the hemodialysis treatment, and a planned water removal volume in the hemodialysis treatment.

According to this embodiment, for example, even when set blood flow velocity is set in a range in which the set blood flow velocity input from the dialysis condition input unit 61 and set in the blood pump 22 and actual blood flow velocity do not coincide with each other, it is possible to calculate a target Kt/V value using actual blood flow velocity corresponding to the set blood flow velocity. Therefore, the target Kt/V value is accurately calculated. In this example, the actual blood flow velocity is calculated from the regression line A between the set blood flow velocity of the blood pump 22 and the venous pressure of the blood return channel 23 on the more downstream side than the dialyzer 20. However, the actual blood flow velocity may be calculated from, for example, the regression line B between the set blood flow velocity of the blood pump 22 and the pressure of the blood supply channel 21.

Next, calculation of a body fluid volume by the body fluid volume calculating unit 60, the mathematical model concerning urea kinetics used for calculation of Kt/V by the dialysis dose calculating unit 62, and an analysis method of the mathematical model in the embodiment explained above are explained.

Figure 13:
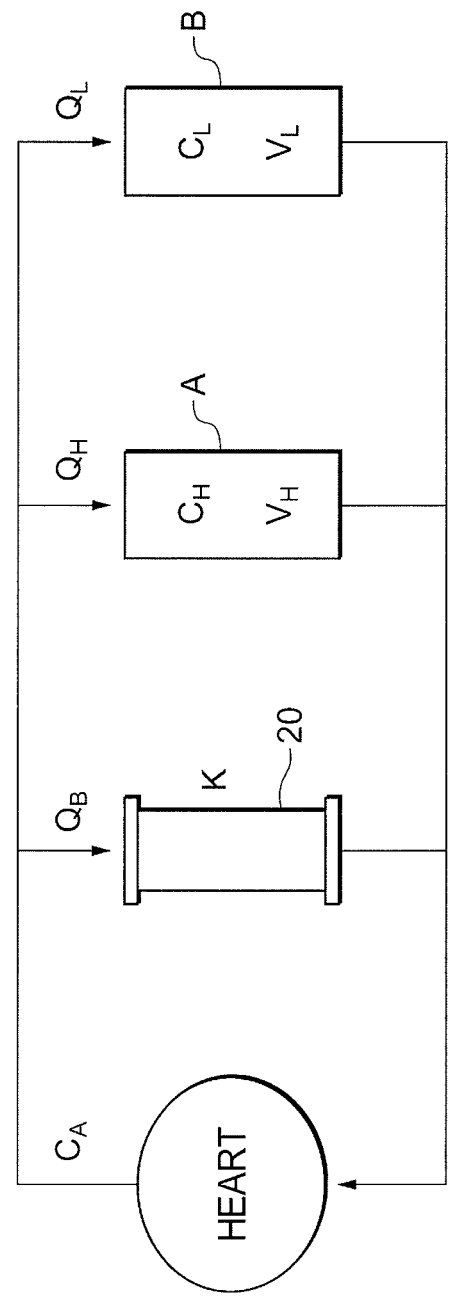
FIG. 13 is a schematic explanatory diagram for explaining a regional blood flow model.

Since a regional blood flow model considered to be most approximate to a dialysis patient body among various urea kinetic models, the regional blood flow model was adopted in the embodiment explained above. A schematic diagram for explaining the regional blood flow model is shown in FIG. 13 (in FIG. 13, K: a urea clearance in the dialyzer 20, $C_A$: urea concentration in the artery, $C_H$: urea concentration in a high-blood flow organ, $C_L$: urea concentration in a low-blood flow organ, $V_H$: a water volume of the high-blood flow organ, $V_L$: a water volume of the low-blood flow organ, $Q_B$: extracorporeally circulating blood flow velocity, $Q_H$: blood flow velocity in the high-blood flow organ, $Q_L$: blood flow velocity in the low-blood flow organ, A: the high-blood flow organs, and B: the low-blood flow organs). The regional blood flow model is a urea kinetic model based on a theory that a organs in the human body are divided into a organ group(which is referred to as low-blood flow organs B) including muscles, skins, etc in which a blood flow is small although a water content volume is large and a organ group (which is referred to as high-blood flow organs A) including digestive organs such as the liver and the intestines) in which a water content volume is small and a blood flow is large. In the regional blood flow model, 15% of internally circulating blood, which is a blood volume obtained by subtracting extracorporeally circulating blood from the cardiac output circulates in the low-blood flow organs B and the remaining 85% circulates in the high-blood flow organs A, and on the other hand, 80% of a body fluid volume is distributed in the low-blood flow organ B and the remaining 20% is distributed in the high-blood flow organs A. Concerning these points, the description of Non-Patent Literature 1 can be referred to.

The regional blood flow model can be rewritten as a form of a mathematical model as shown below.

$$d\,M_H(t)/dt + d\,M_L(t)/dt = -K \times C_A(t) \tag{1}$$

$$M_H(t) = C_H(t) \times V_H(t) \tag{2}$$

$$M_L(t) = C_L(t) \times V_L(t) \tag{3}$$

$$d\,M_H(t)/dt = [C_A(t) - C_H(t)] \times Q_H \tag{4}$$

$$d\,M_L(t)/dt = [C_A(t) - C_L(t)] \times Q_L \tag{5}$$

where, $M_H(t)$ represents an amount of urea in the high-blood flow organs A at time t and $M_L(t)$ represents an amount of urea in the low-blood flow organs B at time t.

$$d\,V_T(t)/dt = -F \tag{6}$$

$$V_H(t) = 0.2 V_T(t) \tag{7}$$

$$V_L(t) = 0.8 V_T(t) \tag{8}$$

$$Q_H = 0.85(Q_A - Q_B) \tag{9}$$

$$Q_L = 0.15(Q_A - Q_B) \tag{10}$$

where, F represents a water removal speed, $V_T(t)$ represents a body fluid volume at time t, and $Q_A$ represents a cardiac output.

When the mathematical regional blood flow model is analyzed in order to calculate a body fluid volume in the body fluid volume calculating unit 60, first, at the start of hemodialysis treatment (t=0), since urea kinetics in a body is in an equilibrium state, it is assumed that both of urea concentration of the low-blood flow organs B and urea concentration of the high-blood flow organs A are equal to the urea concentration in arterial blood. In other words, measured serum urea concentration at the start of the hemodialysis treatment is set as an initial value [$C_A(0)$] of the urea concentration in the arterial blood in the mathematical regional blood flow model, and at the same time, set as initial values of urea concentration [$C_L(0)$] of the low-blood flow organs B and urea concentration [$C_H(0)$] of the high-blood flow organs A as well. Next, a urea clearance in the dialyzer 20 is calculated according to a formula of Expression 1 shown below from blood flow velocity of extracorporeally circulating blood, dialysis fluid flow velocity, and a mass-transfer area coefficient of the dialyzer. In the formula, $Q_B$(mL/minute) represents blood flow velocity, $Q_D$(mL/minute) represents dialysis fluid flow velocity, $K_0A$ represents a mass-transfer area coefficient (mL/minute) of the dialyzer 20, and K(mL/minute) represents a urea clearance of the dialyzer 20.

$$K = \frac{1 - \exp\left[KoA\left(\frac{1}{Q_B} - \frac{1}{Q_D}\right)\right]}{\frac{1}{Q_B} - \frac{1}{Q_D}\exp\left[KoA\left(\frac{1}{Q_B} - \frac{1}{Q_D}\right)\right]} \quad \text{[Expression 1]}$$

The urea clearance (K) and the water removal speed (F) calculated by dividing an water removal volume during hemodialysis treatment by a dialysis treatment time are treated as constants and an average value of 4,000 mL/minute is given to the cardiac output and a provisional value is given to the body fluid volume [VT(0)] to analyze the mathematical regional blood flow model to thereby calculate urea concentration in arterial blood [$C_A(Td)$] at the end of dialysis treatment. Td represents the dialysis treatment time.

When the urea concentration in arterial blood [$C_A(Td)$] at the end of the dialysis treatment at the provisional body fluid volume calculated as explained above is different from measured serum urea concentration at the end of the dialysis treatment, the provisional body fluid volume is slightly changed and urea concentration in arterial blood [$C_A(Td)$] at the end of the dialysis treatment at the new provisional body fluid volume is calculated. The same operation is repeated until the calculated urea concentration in arterial blood [$C_A(Td)$] at the end of the dialysis treatment coincides with the measured serum urea concentration at the end of the dialysis treatment. When the calculated urea concentration in arterial blood [$C_A(Td)$] at the end of the dialysis treatment coincides with the measured serum urea concentration at the end of the dialysis treatment at last, a body fluid volume at that point is adopted as a true body fluid volume.

Further, in order to calculate Kt/V by analyzing the mathematical regional blood flow model in the dialysis dose calculating unit 62 using the body fluid volume calculated by analyzing the mathematical regional blood flow model in the body fluid volume calculating unit 60, first, the initial value [$C_A(0)$] of the urea concentration in the arterial blood, the initial value [$C_L(0)$] of the urea concentration of the low-blood flow organs B, and the initial value [$C_H(0)$] of the urea concentration of the high-blood flow organs A at the start of the hemodialysis treatment (t=0) are provisionally set to 1 mg/mL. All of the urea concentration in the arterial blood, the urea concentration of the low-blood flow organs B, and the urea concentration of the high-blood flow organs A are set equal at the start of the hemodialysis treatment in this way. This is based on the fact that urea kinetics is in the stable state in the patient body at the start of the hemodialysis treatment.

Next, a urea clearance in the dialyzer 20 is calculated from the input dialysis fluid flow velocity, the input blood flow velocity, and the overall mass-transfer area coefficient of the dialyzer 20 according to Formula 1 above. The urea concentration in arterial blood [$C_A(Td)$] at the end of the dialysis treatment is calculated, in the case that the initial value [$C_A(0)$] of the urea concentration in the arterial blood, the initial value [$C_L(0)$] of the urea concentration of the low-blood flow organs B, and the initial value [$C_H(0)$] of the urea concentration of the high-blood flow organs A at the start of the hemodialysis treatment (t=0) are provisionally set to 1 mg/mL, by analyzing the mathematical regional blood flow model, from the urea clearance calculated in this way, the body fluid volume calculated by analyzing the mathematical regional blood flow model, the water removal volume, and the hemodialysis treatment time. A Kt/V value is calculated according to a formula of Expression 2 shown below from a ratio of the calculated urea concentration in arterial blood [$C_A(Td)$] at the end of the dialysis treatment and the initial value [$C_A(0)$=1 mg/mL] of the urea concentration in the arterial blood.

$$Kt/V = -\ln\left(\frac{C_A(Td)}{C_A(0)} - 0.008\ Td\right) + \left(4 - 3.5\frac{C_A(Td)}{C_A(0)}\right) \cdot F \times Td/BW(Td) \quad \text{[Expression 2]}$$

It is assumed that, until an arbitrary point during the hemodialysis treatment, a hemodialysis treatment is executed at blood flow velocity of 200 mL/minute, which is general blood flow velocity in a dialysis patient, set in advance before the start of the hemodialysis treatment, and dialysis fluid flow velocity of 500 mL/minute, which is general dialysis fluid flow velocity in the dialysis patient, also set in advance before the start of the hemodialysis treatment, and then the blood flow velocity and/or the dialysis fluid flow velocity is changed at the point during the hemodialysis treatment. In this case, by analyzing the mathematical regional blood flow model, first, urea concentration in arterial blood [$C_A(T)$], an initial value [$C_L(T)$] of the urea concentration of the low-blood flow organs B, and an initial value [$C_H(T)$] of the urea concentration of the high-blood flow organs A at the point during the hemodialysis treatment are calculated, where the initial value [$C_A(0)$] of the urea concentration in the arterial blood, the initial value [$C_L(0)$] of the urea concentration of the low-blood flow organs B, and the initial value [$C_H(0)$] of the urea concentration of the high-blood flow organs A at the start of the hemodialysis treatment (t=0) are provisionally set to 1 mg/mL.

Next, the urea concentration in arterial blood [$C_A(T)$], the urea concentration [$C_L(T)$] of the low-blood flow organs B, and the urea concentration [$C_H(T)$] of the high-blood flow organs A at the point during the hemodialysis treatment are respectively set as new initial values of the urea concentration in arterial blood, and on the basis of these initial values, the urea concentration in arterial blood [$C_A(Td')$] at the end of the hemodialysis treatment is calculated. A Kt/V value is calculated according to Formula 2 from a ratio of the calculated urea concentration in arterial blood [$C_A(Td')$] at the end of the hemodialysis treatment and the original initial value [$C_A(0)$= 1 mg/mL] of the urea concentration in the arterial blood.

In this embodiment, in sixteen dialysis patients, body fluid volumes were calculated by the body fluid volume calculating means 11 in a day of a regular blood sampling, and at the start of hemodialysis treatment executed fifty-three times in total after the regular blood sampling day, Kt/V values were calculated by the dialysis dose calculating unit 62 using the body fluid volumes and necessary parameters.

Figure 14:
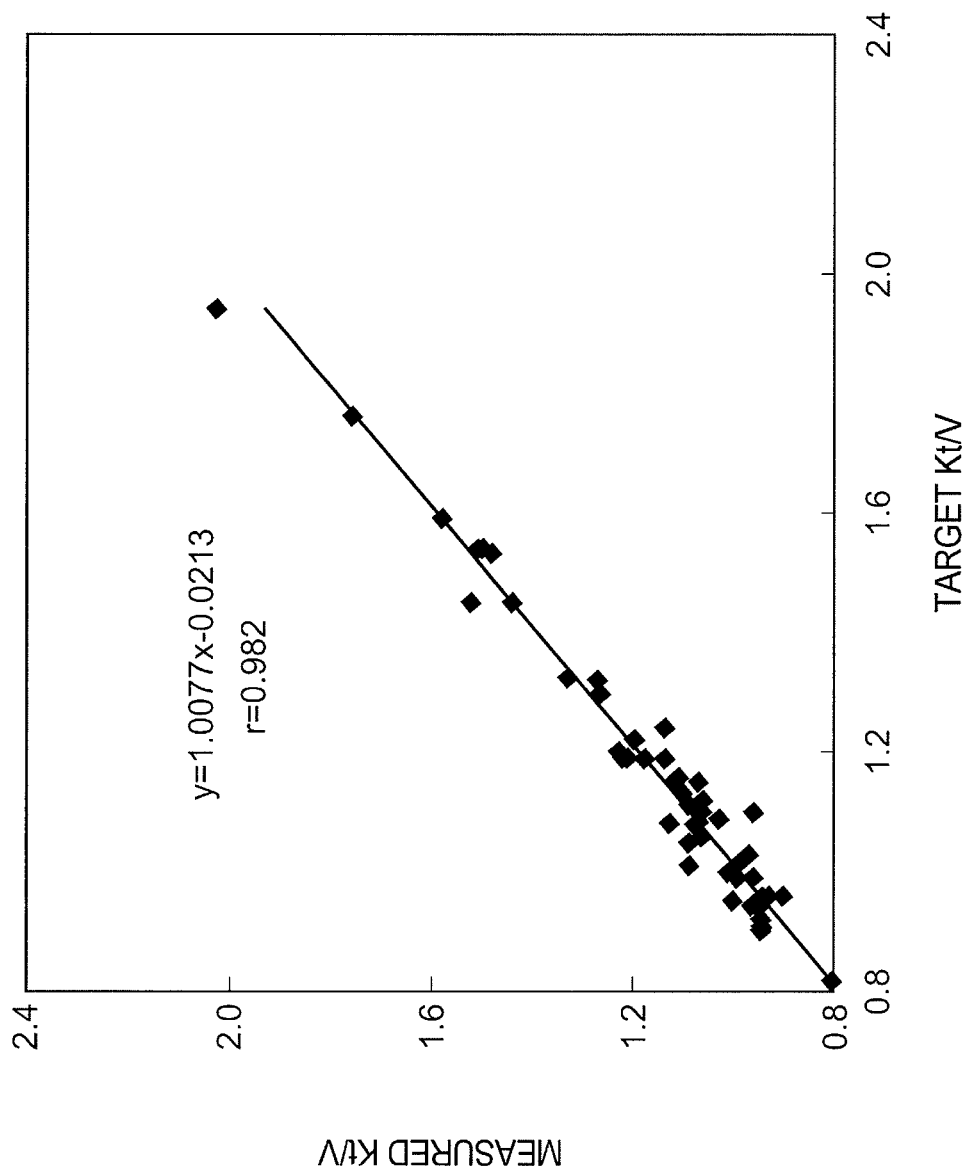
FIG. 14 is a graph showing a relation between a target Kt/V value and a measured Kt/V value.

In FIG. 14, a relation between Kt/V calculated by the dialysis dose calculating unit 62 on the basis of blood flow velocity and dialysis fluid flow velocity input from the dialysis condition input unit 61 and measured Kt/V is shown. The measured Kt/V means Kt/V calculated by the formula of Expression 2 from measured serum urea concentration at the start of the hemodialysis treatment and measured serum urea concentration at the end of the hemodialysis. As is evident from FIG. 14, there was a strong linear correlation having a correlation coefficient of 0.982 and a regression equation of Y=1.0077X+0.0213 between Kt/V(X) calculated by the dialysis dose calculating unit 62 and measured Kt/V(Y). This indicates that the Kt/V calculated by the dialysis dose calculating unit 62 coincides with the measured Kt/V.

The preferred embodiment of the present invention has been explained with reference to the accompanying drawings. However, the present invention is not limited to such an example. It is evident that those skilled in the art could devise various modification examples or alteration examples within the category of the idea described in the patent claims. It is understood that the modification examples or the alteration examples naturally belong to the technical scope of the present invention.

For example, in the embodiment, the regional blood flow model is used as the model concerning urea kinetics. However, the model concerning urea kinetics used in the present invention is not limited to the regional blood flow model. Any model such as a generally-known single-pool model concerning urea kinetics may be used as long as the model can mathematically represent kinetics of urea in the human body. In the embodiment, the Kt/V value is used as the index of a dialysis dose. However, the index of a dialysis dose used in the present invention is not limited to the Kt/V value. Any index may be used as long as the index is calculated from serum urea concentrations at the start and at the end of dialysis treatment.

Further, for example, in the embodiment, after the end of the hemodialysis treatment on the regular blood sampling day, the body fluid volume, which is the total volume of water in the body of the patient, is directly calculated, by analyzing the mathematical model concerning urea kinetics, from the measured serum urea concentration at the start of the hemodialysis treatment and the measured serum urea concentration at the end of the hemodialysis treatment, the dialysis treatment time of the hemodialysis treatment, the water removal volume during the hemodialysis treatment, the blood flow velocity in the hemodialysis treatment, the dialysis fluid flow velocity in the hemodialysis treatment, and the overall mass-transfer area coefficient of the dialyzer used for the hemodialysis treatment. However, the present invention is not always limited to this. From parameters relating to a body fluid volume, by analyzing the mathematical model concerning urea kinetics, the body fluid volume can be calculated.

In the embodiment, the upper limit value and the lower limit value of the blood flow velocity are set. However, an upper limit value and a lower limit value of the dialysis fluid flow velocity may be set. A dialysis flow rate error, for example, a guarantee range margin of 10% may be set on the basis of a result of an in-vitro dialysis fluid circulation experiment, which is performed using the hemodialysis system 1 including the dialysis fluid pump 25, at a design stage in advance and a numerical value of the dialysis flow rate error may be used for the upper limit value and the lower limit value of the dialysis fluid flow velocity.

REFERENCE SIGNS LIST 1 hemodialysis system
10 hemodialysis executing unit
11 control unit
20 dialyzer
21 blood supply channel
22 blood pump
23 blood return channel
24 dialysis fluid supply channel
25 dialysis fluid pump
26 dialysis fluid discharge channel
27 water removing means
31 artery-side pressure sensor
41 vein-side pressure sensor
60 body fluid volume calculating unit
61 dialysis condition input unit
62 dialysis dose calculating unit
63 dialysis dose display unit
64 blood flow velocity upper limit value calculating unit
80 fixed condition input unit
81 variable condition input unit
90 blood flow velocity adjustment button
91 dialysis fluid flow velocity adjustment button

What is claimed is:
1. A hemodialysis system comprising:
  a hemodialysis executing unit including:
    a dialyzer configured to purify blood,
    a blood supply channel for supplying blood extracted from a body to the dialyzer,
    a blood pump provided in the blood supply channel for delivering the blood to the dialyzer,
    a blood return channel for returning the blood purified by the dialyzer to the body, a dialysis fluid supply channel for supplying dialysis fluid to the dialyzer,
    a dialysis fluid pump provided in the dialysis fluid supply channel for supplying the dialysis fluid to the dialyzer, and
    a dialysis fluid discharge channel for discharging, from the dialyzer, the dialysis fluid used for purifying the blood in the dialyzer;
  a body fluid volume calculator configured to calculate, by analyzing a mathematical model concerning urea kinetics, a body fluid volume, which is a total volume of water present in the body of a patient, from measured serum urea concentration at a start of a first hemodialysis treatment and measured serum urea concentration at an end of the first hemodialysis treatment, a dialysis treatment time of the first hemodialysis treatment, a water removal volume in the first hemodialysis treatment, blood flow velocity in the first hemodialysis treatment, dialysis fluid flow velocity in the first hemodialysis treatment, and a mass-transfer area coefficient of the dialyzer used for the first hemodialysis treatment;
  a dialysis condition input with which blood flow velocity and dialysis fluid flow velocity in a second hemodialysis treatment, performed after the first hemodialysis treatment, can be input and input values of the blood flow velocity and the dialysis fluid flow velocity can be adjusted, wherein a blood flow velocity adjustment button for adjusting blood flow velocity in the hemodialysis treatment and a dialysis fluid flow velocity adjustment button for adjusting dialysis fluid flow velocity in the hemodialysis treatment are provided in the dialysis condition input;

a dialysis dose calculator configured to calculate, when the blood flow velocity and the dialysis fluid flow velocity are input to the dialysis condition input, by analyzing the mathematical model concerning urea kinetics, a dialysis dose of the second hemodialysis treatment from the input blood flow velocity and the input dialysis fluid flow velocity, a mass-transfer area coefficient of the dialyzer used for the second hemodialysis treatment, a body fluid volume calculated by the body fluid volume calculator, a planned treatment time of the second hemodialysis treatment, and a planned water removal volume in the second hemodialysis treatment; and a dialysis dose display configured to display the hemodialysis dose calculated by the dialysis dose calculator, wherein the blood flow velocity and the dialysis fluid flow velocity input from the blood flow velocity adjustment button and the dialysis fluid flow velocity adjustment button are acquired by the dialysis dose calculator on a real time basis and are displayed on the dialysis dose display on a real time basis.

2. The hemodialysis system according to claim 1, further comprising an actual blood flow velocity calculator configured to calculate actual blood flow velocity, which is obtained when the blood flow velocity input in the dialysis condition input is set as set blood flow velocity, from a regression line between set blood flow velocity set in the blood pump during the second hemodialysis treatment and pressure of one of the blood supply channel and the blood return channel, wherein the dialysis dose calculator calculates the dialysis dose using the actual blood flow velocity calculated by the actual blood flow velocity calculator.

3. The hemodialysis system according to claim 1, wherein the blood flow velocity and the dialysis fluid flow velocity can be input to the dialysis condition input in a stepwise manner, the dialysis dose calculator calculates the dialysis dose at each of the input steps of the blood flow velocity and the dialysis fluid flow velocity, and the dialysis dose display displays the dialysis dose at each of the input steps.

4. The hemodialysis system according to claim 3, wherein at least an upper limit value or a lower limit value that can be input is able to be set in the dialysis condition input concerning at least the blood flow velocity or the dialysis fluid flow velocity.

5. The hemodialysis system according to claim 4, wherein a range in which the blood flow velocity can be set is set in a range in which set blood flow velocity set in the blood pump during the second hemodialysis treatment and actual blood flow velocity coincide with each other.

6. The hemodialysis system according to claim 5, wherein a value of the set blood flow velocity at a time when arterial pressure of the blood supply channel on an upstream side of the blood pump deviates from a regression line between the set blood flow velocity of the blood pump and the arterial pressure is calculated, the arterial pressure being measured while changing the set blood flow velocity, and wherein the calculated value of the set blood flow velocity is set as the upper limit value of the range in which the blood flow velocity can be input.

7. The hemodialysis system according to claim 4, wherein a value of the set blood flow velocity at a time when venous pressure of the blood return channel downstream from the dialyzer deviates from a regression line between the set blood flow velocity of the blood pump and the venous pressure is calculated, the venous pressure being measured while changing the set blood flow velocity, and wherein the calculated value of the set blood flow velocity is set as the upper limit value of the range in which the blood flow velocity can be input.

8. The hemodialysis system according to claim 4, wherein the upper limit value of the range in which the blood flow velocity can be input is an upper limit value of the blood flow velocity for not causing a jet stream in a vein-side puncture needle during the second hemodialysis treatment.

9. The hemodialysis system according to claim 4, further comprising a blood flow velocity upper limit value calculator configured to calculate an upper limit value of the blood flow velocity in the first hemodialysis treatment according to a method of at least (a) or (b), wherein the method (a) is a method of measuring, while changing set blood flow velocity of the blood pump, venous pressure of the blood return channel downstream from the dialyzer, calculating a value of the set blood flow velocity at a time when the venous pressure deviates from a regression line between the set blood flow velocity of the blood pump and the venous pressure, and setting the calculated value of the set blood flow velocity as the upper limit value of the blood flow velocity, the method (b) is a method of measuring, while changing the set blood flow velocity of the blood pump, arterial pressure of the blood supply channel on an upstream side of the blood pump, calculating a value of the set blood flow velocity at a time when the arterial pressure deviates from a regression line between the set blood flow velocity of the blood pump and the arterial pressure, and setting the calculated value of the set blood flow velocity as the upper limit value of the blood flow velocity, and the upper limit value of the blood flow velocity calculated by the blood flow velocity upper limit value calculator is set in the dialysis condition input.

10. The hemodialysis system according to claim 4, further comprising a blood flow velocity upper limit value calculator configured to calculate an upper limit value of the blood flow velocity in the first hemodialysis treatment according to a method of at least (a) or (b), wherein the method (a) is a method of measuring, while changing set blood flow velocity of the blood pump, venous pressure of the blood return channel downstream from the dialyzer, calculating a value of the set blood flow velocity at a time when the venous pressure deviates from a regression line between the set blood flow velocity of the blood pump and the venous pressure, wherein the method (b) is a method of measuring, while changing the set blood flow velocity of the blood pump, arterial pressure of the blood supply channel on an upstream side of the blood sums calculating a value of the set blood flow velocity at a time-when the arterial pressure deviates from a regression line between the set blood flow velocity of the blood pump and the arterial pressure, wherein the blood flow velocity upper limit value calculator sets a smaller value of the values of the set blood flow velocity calculated by the methods (a) and (b) as the upper limit value of the blood flow velocity, and wherein the upper limit value of the blood flow velocity calculated by the blood flow velocity upper limit value calculator is set in the dialysis condition input.

11. The hemodialysis system according to claim 3, further comprising an actual blood flow velocity calculator configured to calculate actual blood flow velocity, which is obtained when the blood flow velocity input in the dialysis condition input is set as set blood flow velocity, from a regression line between set blood flow velocity set in the blood pump during the second hemodialysis treatment and pressure of one of the blood supply channel and the blood return channel, wherein
the dialysis dose calculator calculates the dialysis dose using the actual blood flow velocity calculated by the actual blood flow velocity calculator.

12. The hemodialysis system according to claim 1, wherein at least an upper limit value or a lower limit value that can be input is able to be set in the dialysis condition input concerning at least the blood flow velocity or the dialysis fluid flow velocity.

13. The hemodialysis system according to claim 12, wherein a range in which the blood flow velocity can be set is set in a range in which set blood flow velocity set in the blood pump during the second hemodialysis treatment and actual blood flow velocity coincide with each other.

14. The hemodialysis system according to claim 13, wherein a value of the set blood flow velocity at a time when arterial pressure of the blood supply channel on an upstream side of the blood pump deviates from a regression line between the set blood flow velocity of the blood pump and the arterial pressure is calculated, the arterial pressure being measured while changing the set blood flow velocity, and wherein the calculated value of the set blood flow velocity is set as the upper limit value of the range in which the blood flow velocity can be input.

15. The hemodialysis system according to claim 12, wherein a value of the set blood flow velocity at a time when venous pressure of the blood return channel downstream from the dialyzer deviates from a regression line between the set blood flow velocity of the blood pump and the venous pressure is calculated, the venous pressure being measured while changing the set blood flow velocity, and wherein the calculated value of the set blood flow velocity is set as the upper limit value of the range in which the blood flow velocity can be input.

16. The hemodialysis system according to claim 12, wherein the upper limit value of the range in which the blood flow velocity can be input is an upper limit value of the blood flow velocity for not causing a jet stream in a vein-side puncture needle during the second hemodialysis treatment.

17. The hemodialysis system according to claim 12, further comprising a blood flow velocity upper limit value calculator configured to calculate an upper limit value of the blood flow velocity in the first hemodialysis treatment according to a method of at least (a) or (b), wherein the method (a) is a method of measuring, while changing set blood flow velocity of the blood pump, venous pressure of the blood return channel downstream from the dialyzer, calculating a value of the set blood flow velocity at a time when the venous pressure deviates from a regression line between the set blood flow velocity of the blood pump and the venous pressure, and setting the calculated value of the set blood flow velocity as the upper limit value of the blood flow velocity, the method (b) is a method of measuring, while changing the set blood flow velocity of the blood pump, arterial pressure of the blood supply channel on an upstream side of the blood pump, calculating a value of the set blood flow velocity at a time when the arterial pressure deviates from a regression line between the set blood flow velocity of the blood pump and the arterial pressure, and setting the calculated value of the set blood flow velocity as the upper limit value of the blood flow velocity, and the upper limit value of the blood flow velocity calculated by the blood flow velocity upper limit value calculator is set in the dialysis condition input.

18. The hemodialysis system according to claim 12, further comprising a blood flow velocity upper limit value calculator configured to calculate an upper limit value of the blood flow velocity in the first hemodialysis treatment according to a method of at least (a) or (b), wherein the method (a) is a method of measuring, while changing set blood flow velocity of the blood pump, venous pressure of the blood return channel downstream from the dialyzer, calculating a value of the set blood flow velocity at a time when the venous pressure deviates from a regression line between the set blood flow velocity of the blood pump and the venous pressure, wherein the method (b) is a method of measuring, while changing the set blood flow velocity of the blood pump, arterial pressure of the blood supply channel an upstream side of the blood sums calculating a value of the set blood flow velocity at a time when the arterial pressure deviates from a regression line between the set blood flow velocity of the blood pump and the arterial pressure, wherein the blood flow velocity upper limit value calculator sets a smaller value of the values of the set blood flow velocity calculated by the methods (a) and (b) as the upper limit value of the blood flow velocity, and wherein the upper limit value of the blood flow velocity calculated by the blood flow velocity upper limit value calculator is set in the dialysis condition input.

* * * * *